United States Patent [19]
Hayashi et al.

[11] 3,953,435
[45] Apr. 27, 1976

[54] ALDEHYDE DERIVATIVES OF PROSTAGLANDINS

[75] Inventors: Masaki Hayashi; Seiji Kori, both of Takatsuki; Hirofumi Endo, Osaka, all of Japan

[73] Assignee: Ono Pharmaceutical Company, Osaka, Japan

[22] Filed: Dec. 30, 1974

[21] Appl. No.: 537,522

[30] Foreign Application Priority Data

Jan. 10, 1974 United Kingdom................ 1278/74
Oct. 9, 1974 United Kingdom.............. 43777/74
Oct. 22, 1974 United Kingdom.............. 45684/74

[52] U.S. Cl............................. 260/240 R; 260/598
[51] Int. Cl.²...................................... C07C 177/00
[58] Field of Search............ 260/240 R, 598, 468 D

[56] References Cited
UNITED STATES PATENTS

| | | | |
|---|---|---|---|
| 3,504,020 | 3/1970 | Lapidus et al............. | 260/468 D X |
| 3,636,120 | 1/1972 | Pike............................ | 260/468 D |
| 3,749,741 | 7/1973 | Strike et al................... | 260/598 X |
| 3,810,943 | 5/1974 | Jones et al..................... | 260/598 X |
| 3,849,474 | 11/1974 | Nedumparambel et al. | 260/240 R X |
| 3,878,239 | 4/1975 | Hayashi et al............. | 260/240 R X |

*Primary Examiner*—Allen B. Curtis
*Attorney, Agent, or Firm*—Albert H. Graddis; Frank S. Chow

[57] ABSTRACT

Prostaglandin analogues of the formula:-

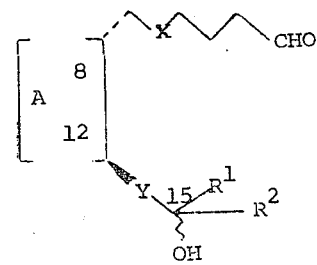

wherein A represents a PGF or PGE grouping, X represents ethylene or cis-vinylene, Y represents ethylene or transvinylene, $R^1$ represents hydrogen or alkyl of 1 to 4 carbon atoms, $R^2$ represents alkyl of 1 to 10 carbon atoms, or alkyl of 1 to 4 carbon atoms substituted by phenyl or cycloalkyl containing from 5 to 7 carbon atoms, or $R^2$ represents a grouping of the formula:-

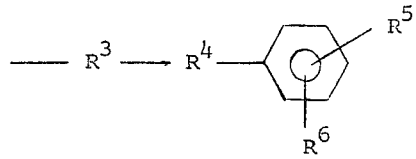

wherein $R^3$ represents alkylene of 1 to 4 carbon atoms, $R^4$ represents oxygen or sulphur or sulphinyl, and $R^5$ and $R^6$ represent hydrogen, halogen, trifluoromethyl, alkyl of 1 to 3 carbon atoms are new compounds possessing pharmacological properties.

26 Claims, No Drawings

ALDEHYDE DERIVATIVES OF PROSTAGLANDINS

This invention relates to new prostaglandin analogues, to a process for their preparation and to pharmaceutical compositions containing them.

Prostaglandins are derivatives of prostanoic acid which has the following formula:

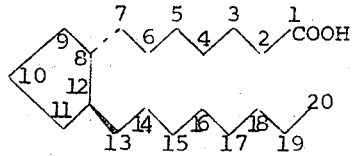

Various types of prostaglandins are known, the types depending inter alia on the structure and substituents on the alicyclic ring. For example, the alicyclic rings of prostaglandins F(PGF) and E(PGE) have the structures:

 and 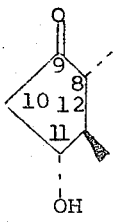

respectively.

Such compounds are sub-classified according to the position of double bond(s) in the side chain(s) attached to the 8- and 12-positions of the alicyclic ring. Thus PG-1 compounds have a trans-double bond between $C_{13}$-$C_{14}$(trans-$\Delta^{13}$), PG-2 compounds have a cis-double bond between $C_5$-$C_6$ and a trans-double bond between $C_{13}$-$C_{14}$(cis-$\Delta^5$, trans-$\Delta^{13}$), and PG-3 compounds have cis-double bonds between $C_5$-$C_6$ and $C_{17}$-$C_{18}$ and a trans-double bond between $C_{13}$-$C_{14}$(cis-$\Delta^5$, trans-$\Delta^{13}$, cis-$\Delta^{17}$). For example, prostaglandin $F_{1\alpha}$ (PGF$_{1\alpha}$) and prostaglandin $E_1$ (PGE$_1$) are characterized by the following structures IV and V.

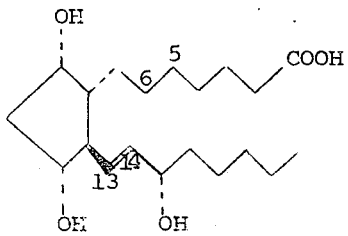

and

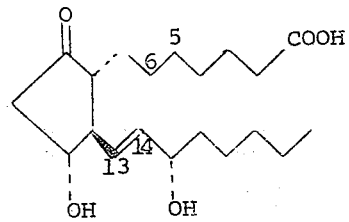

respectively. The structures of PGF$_{2\alpha}$ and PGE$_2$, as members of the PG-2 group, correspond to those of formulae IV and V respectively with a cis-double bond between the carbon atoms in positions 5 and 6. Compounds in which the double bond between the carbon atoms in positions 13 and 14 of members of the PG-1 group is replaced by ethylene(-$CH_2CH_2$-) are known as dihydro-prostaglandins, e.g. dihydro-prostaglandin-F$_{1\alpha}$ (dihydro-PGF$_{1\alpha}$) and dihydro-prostaglandin-E$_1$ (dihydro-PGE$_1$).

Moreover, when one or more methylene groups are added to, or eliminated from, the aliphatic group attached to the 12-position of the alicyclic ring of the prostaglandins the compounds are known, in accordance with the usual rules of organic nomenclature, as $\omega$-homoprostaglandins (methylene group added) or $\omega$-nor-prostaglandins (methylene group eliminated) and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. PGE$_1$ inhibits blood platelet aggregation and also removes the thrombus and prevents thrombosis. PGE's and PGF's have a stimulating effect on smooth muscle and increase the intestinal peristalsis; these actions indicate therapeutic utility on post-operatve ileus and as purgatives. Furthermore, PGE's and PGF's may be used as oxytocics, as abortifacients in the first and second trimesters; in the post-labour abortion of the placenta, and as oral contraceptives because they regulate the sexual cycle of female mammals. PGE's have vasodilator and diuretic activities and are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found that by replacing the carboxy group (—COOH) by a formyl group (—CHO), and optionally replacing a hydrogen atom attached to the carbon atom at the end of the aliphatic group linked to the 12-position of the alicyclic ring of prostaglandins E and F and 15-alkyl analogues thereof by a cycloalkyl group containing 5 to 7 carbon atoms or by a phenyl, phenoxy, phenylthio or phenylsulphinyl group, the pharmacological properties of 'natural' prostaglandins may, in some aspects of their activities, be improved or modified.

The present invention accordingly provides new prostaglandin analogues of the general formula:

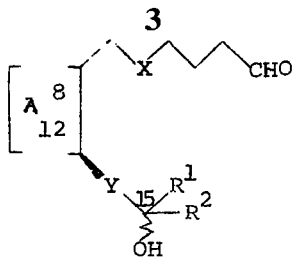

VI

[wherein A represents a grouping of the formula:

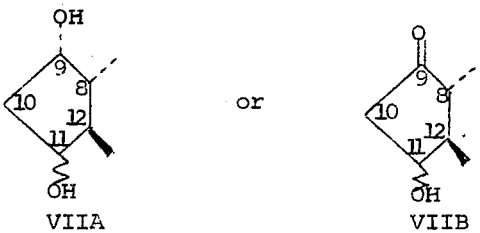

X represents ethylene (i.e. —CH$_2$CH$_2$—) or, preferably, cis-vinylene (i.e. —CH=CH—), Y represents ethylene or, preferably, trans-vinylene, R$^1$ represents a hydrogen atom or a straight- or branched-chain alkyl group containing from 1 to 4 carbon atoms, R$^2$ represents a straight- or branched-chain alkyl group containing from 1 to 10 carbon atoms, preferably an n-pentyl group, or a straight- or branched-chain alkyl group containing from 1 to 4 carbon atoms substituted by a phenyl group or a cycloalkyl group containing from 5 to 7 carbon atoms, for example a cyclopentyl or cyclohexyl group, or R$^2$ represents a grouping of the general formula:-

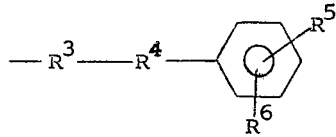

VIII wherein R$^3$ represents a straight- or branched-chain alkylene group containing from 1 to 4 carbon atoms (e.g. methylene, i.e. —CH$_2$—), R$^4$ represents an oxygen or sulphur atom or a sulphinyl group (i.e. —SO—), and R$^5$ and R$^6$ each represent a hydrogen or halogen atom, a trifluoromethyl group or an alkyl group containing from 1 to 3 carbon atoms], and cyclodextrin clathrates of such aldehydes and acetal derivatives thereof with an alcohol or diol. The wavy line ⌇⌇⌇⌇⌇ in general formula VI and in other formulae throughout this specification indicates attachment of the hydroxy group or other group in question in the α- or β-configuration. It will be appreciated that when the hydroxy group attached to the 15-position carbon atom of the compounds of general formula VI is in the α-configuration (as is preferred), the alkyl group R$^1$ will be in the β-configuration, and vice versa.

The present invention is concerned with all compounds of general formula VI in the 'natural' form or its enantiomeric form, or mixtures thereof, more particularly the racemic form consisting of equimolecular mixtures of natural and its enantiomeric form.

All will be apparent to those skilled in the art, the compounds depicted in general formula VI have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carries a hydroxy group on the carbon atom in position 11 (i.e. when the ring is that of formula VIIB) or hydroxy groups in positions 9 and 11 (i.e. when the ring is that of formula VIIA) and further centres of chirality may occur in groups represented by the symbols R$^1$ and R$^2$. The presence of chirality leads, as is well known, to the existence of isomerism. However, the compounds of general formula VI all have such a configuration that the side-chains attached to the ring carbon atoms in the positions identified as 8 and 12 are trans with respect to each other. Accordingly, all isomers of general formula VI, and mixtures thereof, which have those side-chains attached to the ring carbon atoms in positions 8 and 12 in the trans-configuration and have a hydroxy group as depicted in the 15-position are to be considered within the scope of general formula VI.

According to a feature of the present invention, the prostaglandin analogues of general formula VI, wherein the various symbols are as hereinbefore defined, are obtained by the process which comprises hydrolysing a compound of the general formula:-

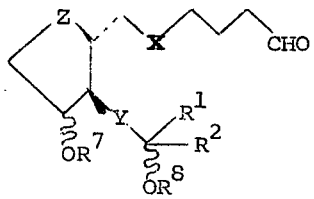

IX (wherein X, Y, R$^1$ and R$^2$ are as hereinbefore defined, Z represents

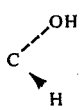

or C=O, R$^7$ represents a 2-tetrahydropyranyl group unsubstituted or substituted by at least one alkyl group, or a 2-tetrahydrofuranyl or 1-ethoxyethyl group and R$^8$ represents a hydrogen atom or a 2-tetrahyropyranyl group unsubstituted or substituted by at least one alkyl group, or a 2-tetrahydrofuranyl or 1-ethoxyethyl group) to convert to a hydroxy group the group OR$^7$ and, when R$^8$ is a 2-tetrahydropyranyl group unsubstituted or substituted by at least one alkyl group, or a 2-tetrahydrofuranyl or 1-ethoxyethyl group, the group $OR^8$.

The groups $OR^7$ and $OR^8$ (when $R^8$ is other than a hydrogen atom) of the compounds of general formula IX may be converted to a hydroxy group by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 60°C. (preferably at a temperature below 45°C.) with an acid mixture, e.g. a mixture of hydrochloric acid and water with tetrahydrofuran or methanol or a mixture of acetic acid, water and tetrahydrofuran.

Compounds of the general formula IX wherein Z represents

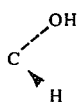

and $R^8$ represents a hydrogen atom, may be prepared by reducing a compound of the general formula:-

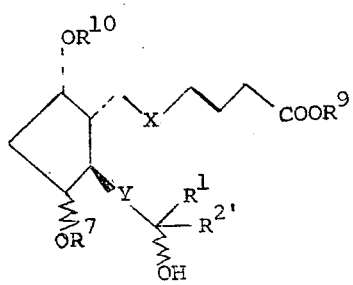

wherein X, Y, $R^1$ and $R^7$ are as hereinbefore defined, $R^9$ represents a straight- or branched-chain alkyl group containing from 1 to 4 carbon atoms, $R^{10}$ represents an alkylcarbonyl group containing from 1 to 4 carbon atoms, and $R^{2'}$ represents a straight- or branched-chain alkyl group containing from 1 to 10 carbon atoms, or a straight- or branched-chain alkyl group containing from 1 to 4 carbon atoms substituted by a phenyl group or a cycloalkyl group containing from 5 to 7 carbon atoms, or $R^{2'}$ represents a grouping of the general formla:

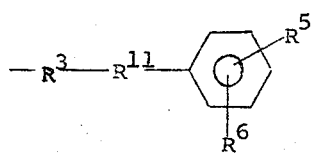

(wherein $R^3$, $R^5$ and $R^6$ are as hereinbefore defined and $R^{11}$ represents an oxygen or sulphur atom) by methods known per se for the conversion of a carboxylic ester group to a formyl group for example by means of diisobutylaluminium hydride.

Compounds of the general formula IX wherein Z represents C=O and $R^1$ represents an alkyl group may be obtained from compounds of the general formula IX wherein Z represents

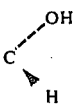

and $R^1$ represents an alkyl group by methods known per se for the conversion of a hydroxy group in the 9-position of a prostaglandin compound to an oxo group, for example by means of a chromic acid solution (e.g. obtained from chromium trioxide, manganese sulphate, sulphuric acid and water) or Jones' reagent.

Compounds of the general formula IX wherein $R^2$ represents a grouping of the general formula VIII, wherein $R^3$, $R^5$ and $R^6$ are as hereinbefore defined, and $R^4$ represents a sulphinyl group may be prepared from compounds of the general formula IX wherein $R^2$ represents a grouping of the general formula VIII, wherein $R^3$, $R^5$ and $R^6$ are as hereinbefore defined, and $R^4$ represents a sulphur atom by oxidation, for example by means of sodium periodate in a mixture of water and a lower alkanol at 0°C. for some hours, e.g. 12 hours.

Compounds of the general formula X wherein $R^1$ represents an alkyl group may be prepared from compounds of general formula:

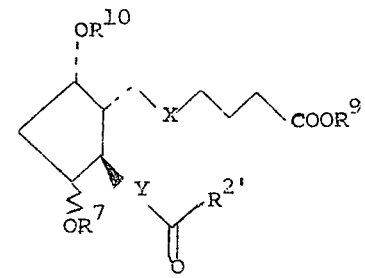

(wherein X, Y, $R^{2'}$, $R^7$, $R^9$ and $R^{10}$ are as hereinbefore defined) by treatment with a Grignard reagent of the general formula:

$$R^1\text{-Mg-Hal} \qquad \text{XIII}$$

(wherein $R^1$ is as hereinbefore defined and Hal represents a halogen atom), e.g. methylmagnesium iodide, in an inert organic solvent, for example tetrahydrofuran or diethyl ether, at a moderately low temperature, for example, at 0°C., followed by hydrolysis of the resulting organomagnesium prostaglandin compound, for example by treatment with water or an aqueous solution of ammonium chloride or an acid, e.g. hydrochloric acid or oxalic acid, to give a mixture of the $\alpha$- and $\beta$-hydroxy epimers of compounds of general formula X. It is sometimes possible that the isomer having the hydroxy group in α-configuration may be separated from the isomer having the hydroxy group in β-configuration by column chromatography of the mixture on silica gel. The separated isomers may be utilized in the procedures herein described to give prostaglandin analogues of general formula VI in which the hydroxy group in position 15 is in α- or β-configuration.

Compounds of the general formula X wherein $R^1$ represents a hydrogen atom may be prepared by reducing to a hydroxy group the oxo group of a compound of general formula XII wherein X, Y, $R^{2'}$, $R^7$, $R^9$ and $R^{10}$ are as hereinbefore defined.

The reduction is suitably effected with excess sodium borohydride in an alkanol containing from 1 to 4 carbon atoms, e.g. methanol, at a low temperature, preferably at −30° to −60°C., or with zinc borohydride in a suitable inert organic solvent, e.g. dimethoxyethane, at a temperature of −10° to 10°C. The product thus obtained is a mixture of isomers in which the hydroxy group at position 15 is in α- or β-configuration respectively. If desired, the isomer having the hydroxy group in α-configuration may be separated from the isomer having the hydroxy group in β-configuration by column chromatography of the mixture on silica gel. The separated isomers may be utilized in the procedures herein described to give prostaglandin analogues of general formula VI in which the hydroxy group in position 15 is in α- or β-configuration.

The processes hreinbefore described may be represented by the series of reactions depicted schematically below in Scheme A.

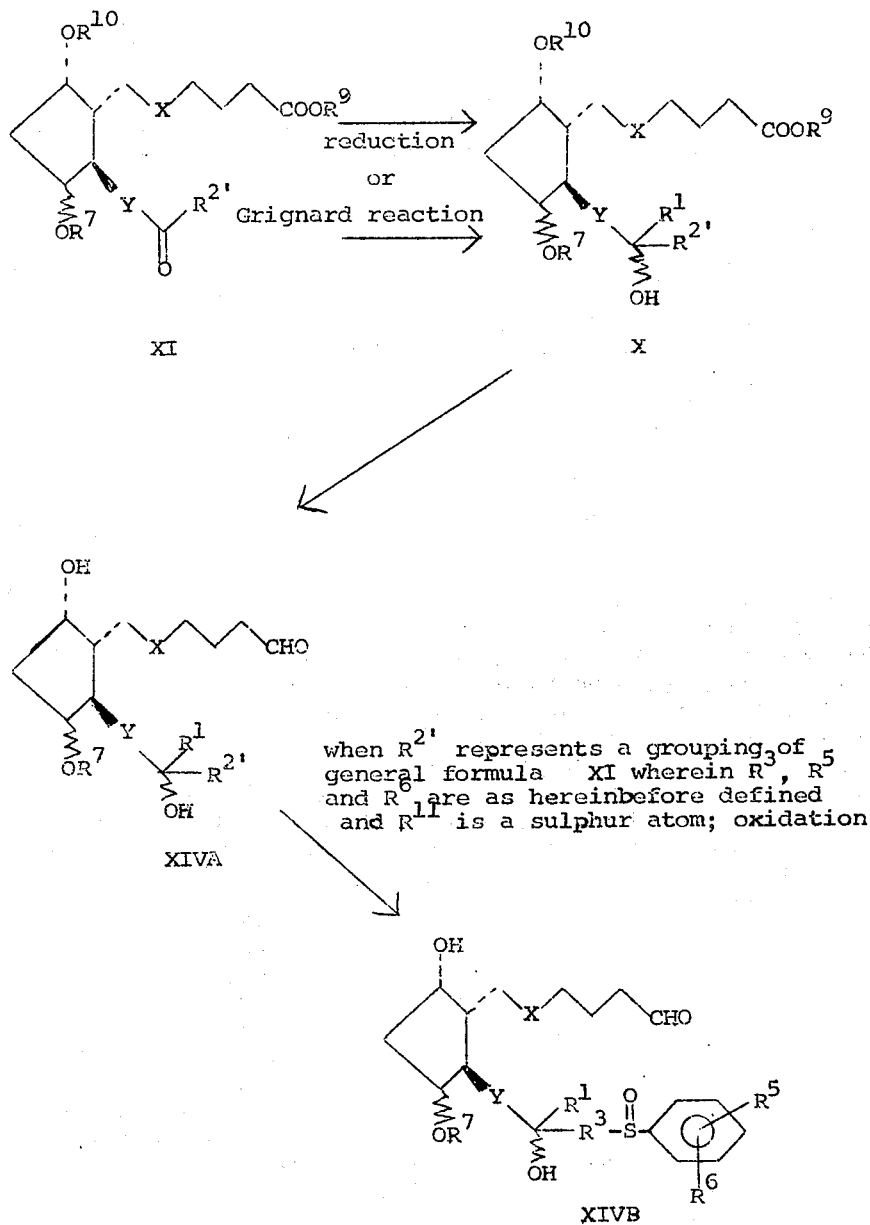

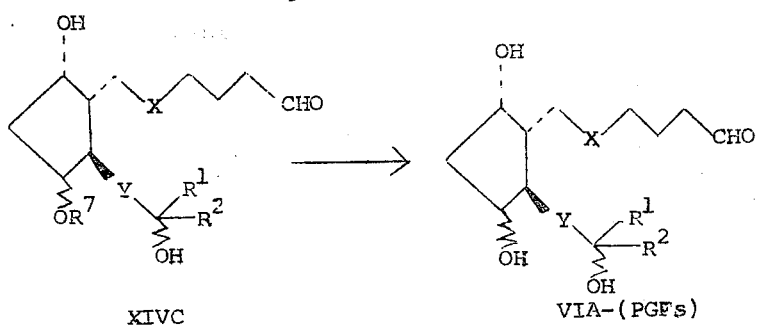

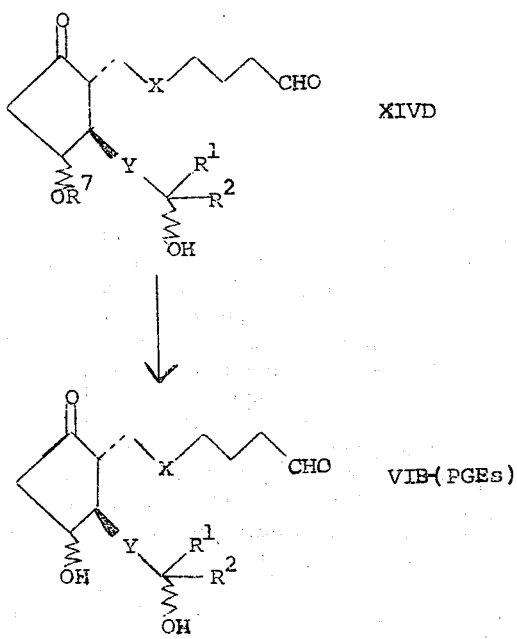

wherein the various symbols are as hereinbefore defined.

Compounds of general formula XII wherein Y represents trans-CH=CH- may be obtained by the Wittig reaction of compounds of the general formula:

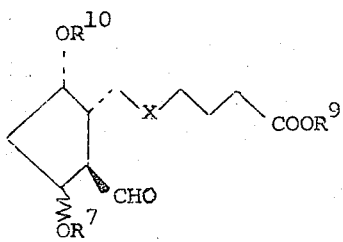

(wherein $R^7$, $R^9$, $R^{10}$ and X are as hereinbefore defined) with the sodio derivative of a dialkyl phosphonate of the general formula:

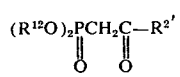   XVI wherein $R^{2'}$ is as hereinbefore defined, and $R^{12}$ represents an alkyl group containing from 1 to 4 carbon atoms. The reaction is preferably effected by suspending sodium hydride in an inert organic solvent, e.g. tetrahydrofuran or 1,2-dimethoxyethane, and adding the dialkyl phosphonate of formula XVI. The resulting sodio derivative of the dialkyl phosphonate may be reacted with the compound of formula XV at 20°C. to 45°C. for one to five hours to form the trans-enone compound of formula XII stereoselectively.

Compounds of general formula XII wherein X represents cis—CH=CH— and Y represents —CH$_2$CH$_2$— may be prepared by selective reduction of the carbonyl conjugated double bond of compounds of general formula XII wherein X and Y represent —CH=CH— by methods known per se, for example by means of lithium 1-pentyne-hydrocuprate (LiCuH-CCC$_3$H$_7$) (see J. Amer. Chem. Soc. 96, 3686 (1974)).

Compounds of general formula XII wherein X and Y represent -CH$_2$CH$_2$-, and $R^{2'}$ is as hereinefore defined except for a group of formula XI wherein $R^{11}$ represents a sulphur atom, may be obtained from compounds of general formula XII wherein Y represents trans-CH=CH-, and $R^{2'}$ is as hereinbefore defined except for a group of formula XI wherein $R^{11}$ represents a sulphur atom, by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter.

Compounds of general formula XII wherein X and Y represent -CH$_2$CH$_2$-, $R^{2'}$ represents a grouping of general formula XI wherein $R^3$, $R^5$ and $R^6$ are as hereinbefore defined and $R^{11}$ represents a sulphur atom, may be obtained by reduction of compounds of general formula XII, wherein Y represents trans-CH=CH-, $R^{2'}$ represents a grouping of general formula XI wherein $R^3$, $R^5$ and $R^6$ are as hereinbefore defined and $R^{11}$ represents a sulphur atom, by means of diimide (NH=NH) prepared from hydrazine and an oxidizing agent, for example a hydroperoxide (J. Chem. Ed. 42, 254 (1965)).

The compounds of general formula XV wherein X. $R^7$, $R^9$ and $R^{10}$ are as hereinbefore defined and the group $OR^7$ is in α-configuration [hereinafter depicted in general formula XVA], used as starting materials in the hereinbefore described procedure, may themselves be prepared by methods known per se from compounds of general formula XVII by the series of reactions depicted schematically below in Scheme B:

SCHEME B

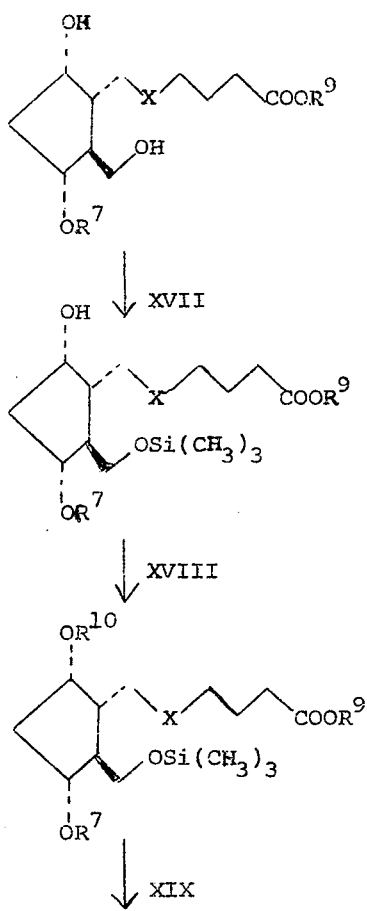

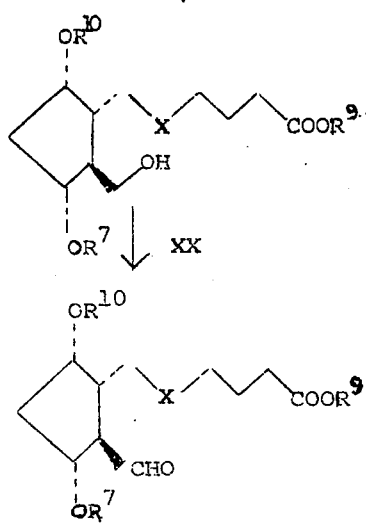

XVA wherein X, $R^7$, $R^9$ and $R^{10}$ are as hereinbefore defined, and preferably $R^{10}$ represents an acetyl group.

Compounds of formula XVIII may be prepared by reacting a compound of formula XVII with trimethylchlorosilane in an inert organic solvent, for example methylene chloride, in the presence of a base, for example pyridine or a tertiary amine, at a low temperature, e.g. at a temperature of −30°C. to 0°C. Compounds of formula XIX may be prepared by reacting a trimethylsilyl ether of formula XVIII with the appropriate acyl chloride or acid anhydride in an inert organic solvent, for example methylene chloride, in the presence of a base, for example pyridine or a tertiary amine, at a low temperature, e.g. at a temperature of 0°C. to 30°C. Compounds of formula XX may be prepared by treating a compound of formula XIX by methods known per se for the removal of the trimethylsilyl group, for example by treatment with an acid; it is preferable not to use a strong acid in order to avoid the risk of the removal of the group $R^7$. The compounds of formula XX may be converted to compounds of formula XVA under mild and neutral conditions, e.g. with chromium trioxide pyridine complex or Jones' reagent and at a moderately low temperature.

The compounds of general formula XVII may themselves be prepared from the known compounds of formula XXI below [the racemic form of the compound of formula XXI is described in J. Amer. Chem. Soc. 91, 5675 (1969) and the natural configuration compound of formula XXI is described in J. Amer. Chem. Soc. 92 397 (1970)] by the series of reactions depicted schematically below in Scheme C:

SCHEME C

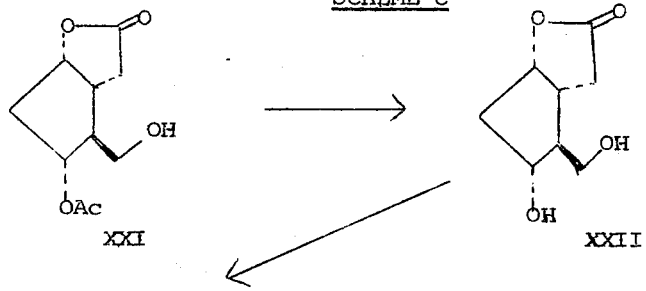

—Continued

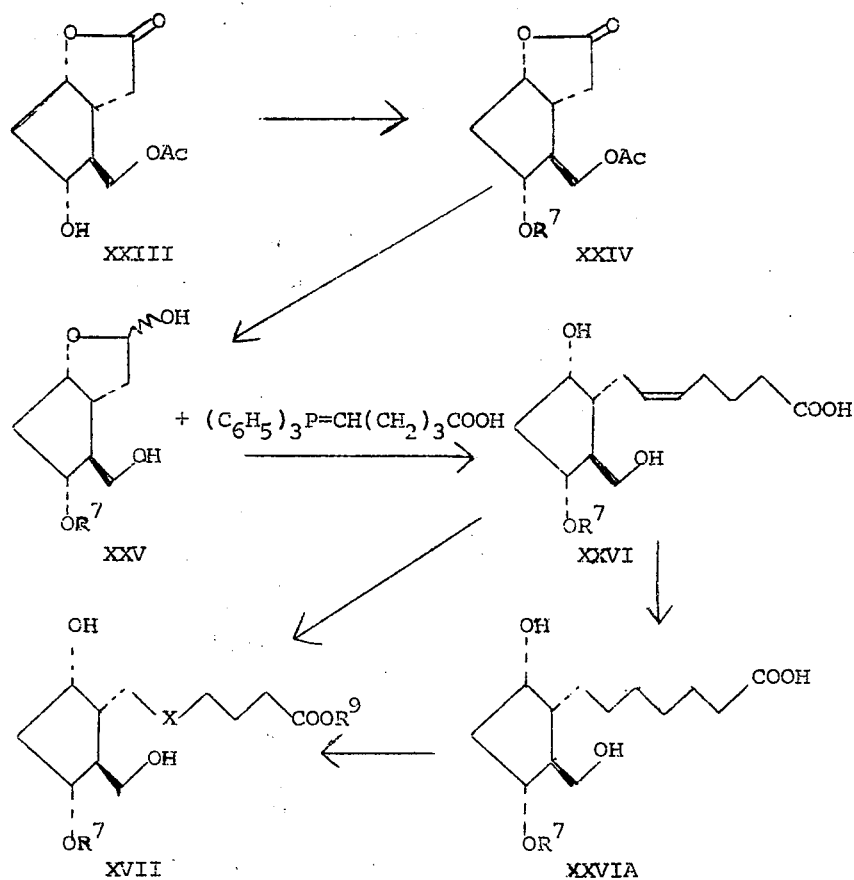

wherein R⁷ and R⁹ are as hereinbefore defined and Ac represents the acetyl group (—COCH₃).

Compounds of formula XXII may be prepared by hydrolysis under alkaline conditions of compounds of formula XXI. Compounds of formula XXIII may be obtained by the acetylation of compounds of formula XXII under mild conditions and may be converted into compounds of formula XXIV by reaction with a dihydropyran, dihydrofuran or ethyl vinyl ether in an inert solvent, e.g. methylene chloride, in the presence of a condensing agent, e.g. p-toluenesulphonic acid. Compounds of formula XXV may be prepared by reducing compounds of formula XXIV with diisobutylaluminium hydride in toluene for about 15 minutes at −60°C. Dimsyl anion, previously prepared from sodium hydride and dimethyl sulphoxide is reacted with 4-carboxy-n-butyl-triphenylphosphonium bromide to form 4-carboxy-n-butylidenetriphenylphosphorane. To that compound is added a compound of formula XXV and the mixture in dimethyl sulphoxide is made to react for 2 hours at room temperature to yield a compound of formula XXVI.

Compounds of formula XXVI may, if desired, be reduced to give compounds of formula XXVIA. Suitably, the reduction may be effected by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter. Compounds of formula XXVI or XXVIA are then reacted with a diazoalkane in a suitable inert solvent e.g. diethyl ether, to give compounds of formula XVII.

The compounds of general formula XV wherein X represents cis-vinylene, R⁷, R⁹ and R¹⁰ are as hereinbefore defined and the group OR⁷ is in β-configuration, which may be used as starting materials in the hereinbefore described procedures, may themselves be prepared by the series of reactions depicted in Schemes B and C but replacing the compounds of formulas XXI by compounds of the formula:

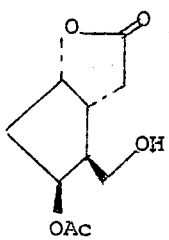

XXVII wherein Ac is as hereinbefore defined.

A method for the preparation of the bicyclo-octane starting materials of formula XXVII, wherein Ac is as hereinbefore defined, utilizing known procedures may be represented by the series of reactions depicted schematically below in Scheme D (cf. E.J. Corey and Shiro Terashima, Tetrahedron Letters, No. 2 pp. 111–113, 1972):

drofuran at a temperature below −50°C., stirring the reaction mixture at below −50°C. for 1.5 hours, and then stirring for 18 hours at 0°C. to give the desired dialkyl phosphonate of general formula XVI.

The compounds of general formula XXXIII, more particularly those of that formula wherein $R^{2'}$ represents a group of general formula XI, e.g. ethyl 3-tri-

SCHEME D

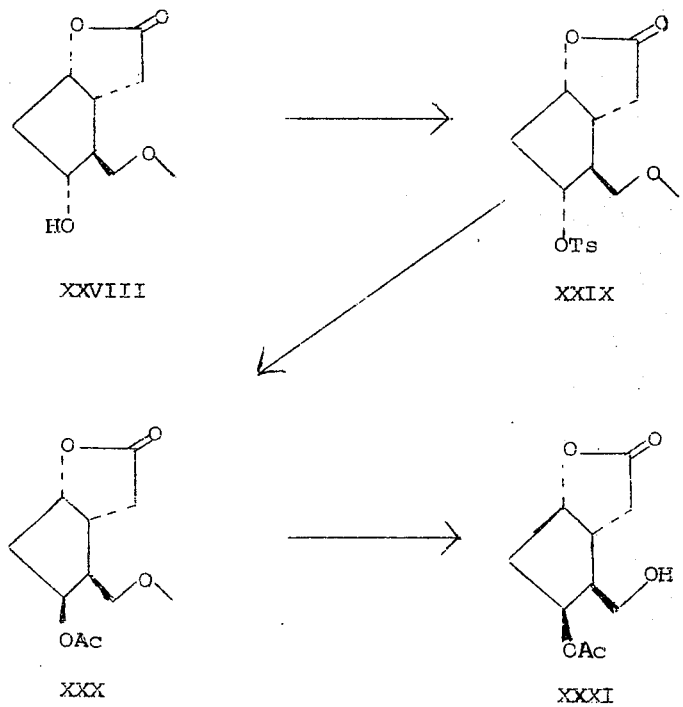

wherein Ac is as hereinbefore defined and Ts represents the tosyl group. The various reactions depicted above in Scheme D may be effected by methods known per se. Compounds of formula XXX may be prepared by reacting compounds of formula XXIX with tetraethylammonium acetate.

The dialkylphosphates of general formula XVI may be prepared by reacting a solution of n-butyllithium in diethyl ether with a solution of a dialkyl methylphosphonate of the formula:

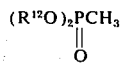   XXXII (wherein $R^{12}$ is as hereinbefore defined), e.g. dimethyl methylphosphonate or diethyl methylphosphonate, at a temperature below −50°C., and then adding dropwise to the reaction mixture a solution of a compound of the general formula:

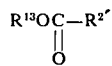   XXXIII (wherein $R^{13}$ represents a lower alkyl group, preferably containing from 1 to 4 carbon atoms, e.g. methyl or ethyl, or $R^{2'}$ is as hereinbefore defined) in tetrahydrofuran at a temperature below −50°C., stirring the reaction mixture at below −50°C. for 1.5 hours, and then stirring for 18 hours at 0°C. to give the desired dialkyl phosphonate of general formula XVI.

fluoromethylphenoxyacetate, ethyl phenoxyacetate, ethyl 3-phenylthio-propionate and ethyl 2-methyl-3-phenylthio-propionate, may be prepared by methods known per se.

Compounds of general formula XII wherein $R^{2'}$ represents a grouping of general formula XI wherein $R^5$ and $R^6$ are as hereinbefore defined, $R^3$ represents a methylene group unsubstituted or substituted by one or two alkyl groups and $R^{11}$ represents a sulphur atom may be prepared from compounds of the general formula:

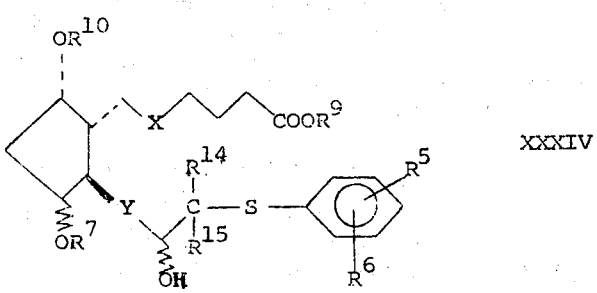

(wherein $R^{14}$ and $R^{15}$ each represent a hydrogen atom or an alkyl group, the total number of carbon atoms present when either or both of $R^{14}$ and $R^{15}$ is or are alkyl groups being three, and X, Y, $R^5$, $R^6$, $R^7$, $R^9$ and R[10] are as hereinbefore defined) by oxidation with chromium trioxide or manganese dioxide.

Compounds of general formula XXXIV may be obtained by the reaction of compounds of the general formula:

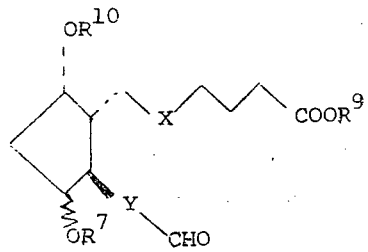

(wherein X, Y, R[7], R[9] and R[10] are as hereinbefore defined) with an organo-metallic compound of the general formula:

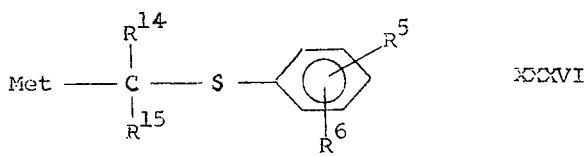

XXXVI wherein R[5], R[6], R[14] and R[15] are as hereinbefore defined, and Met represents a lithium atom or a magnesium halide group. The reaction is preferably effected at a low temperature, preferably below 0°C., more particularly in the case of an organo-lithium compound below −50°C., in an inert organic solvent, e.g. diethyl ether, tetrahydrofuran or n-hexane, for 10 to 60 minutes. The reaction mixture is then hydrolyzed by treatment with water or an aqueous solution of an acid or ammonium chloride to give the compounds of general formula XXXIV.

The compounds of general formula XXXV wherein X represents cis-vinylene, Y represents trans-vinylene and R[7], R[9] and R[10] are as hereinbefore defined, hereafter depicted by general formula XXXVa, are prepared by the sequences of reactions hereinafter depicted schematically in Chart E.

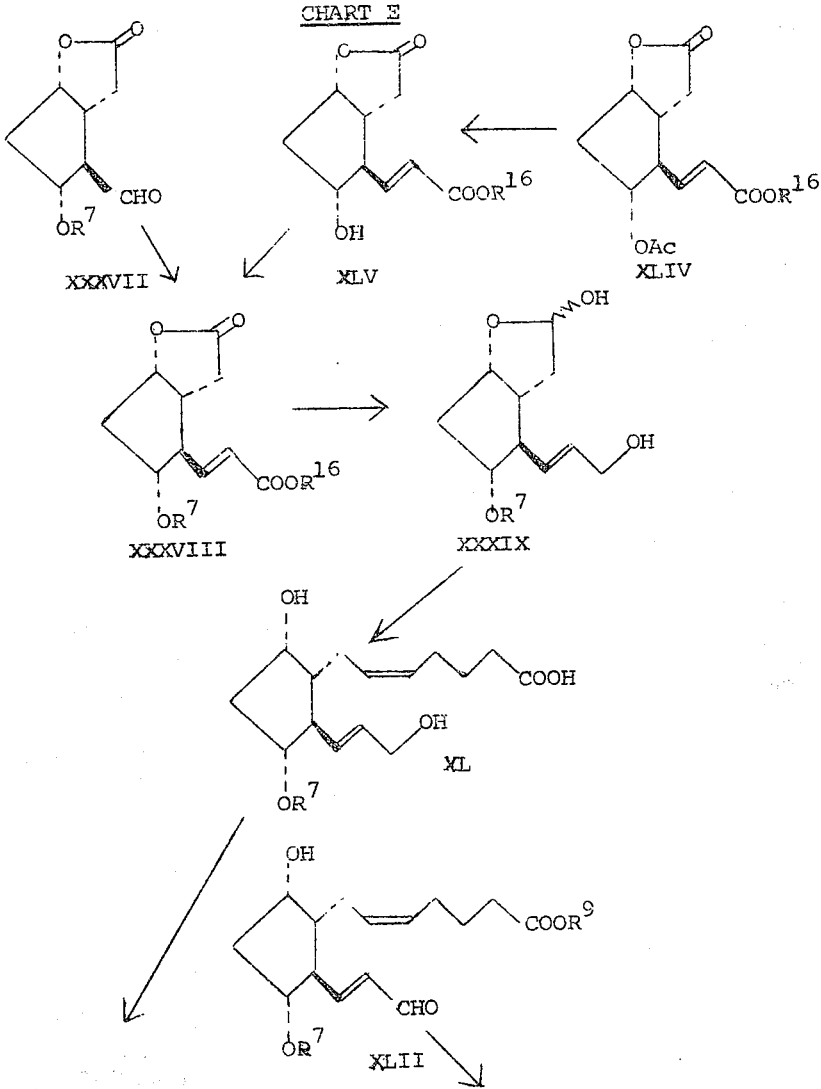

—Continued

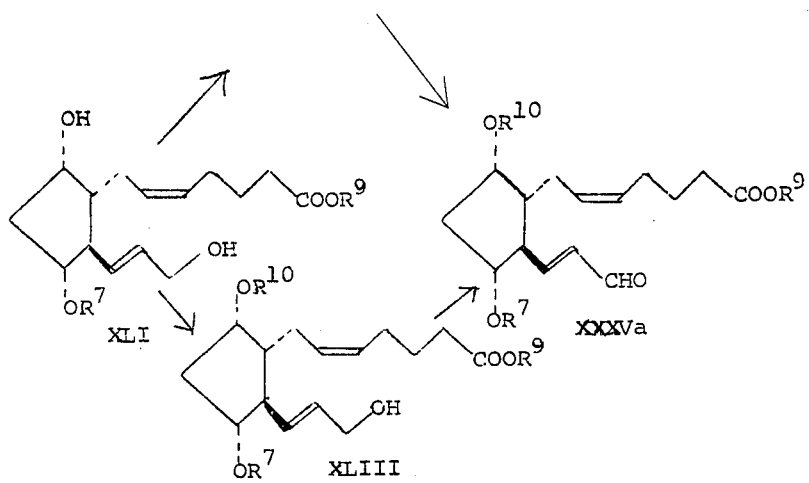

wherein $R^{16}$ represents a straight- or branched-chain alkyl group containing 1 to 4 carbon atoms, and $R^7$, $R^9$ and $R^{10}$ are as hereinbefore defined.

Referring to Chart E, the starting compounds of general formula XXXVII may be prepared from the compounds of general formula XLVI hereafter by the series of reactions depicted schematically below in Chart F, wherein $R^7$ is as hereinbefore defined.

CHART F

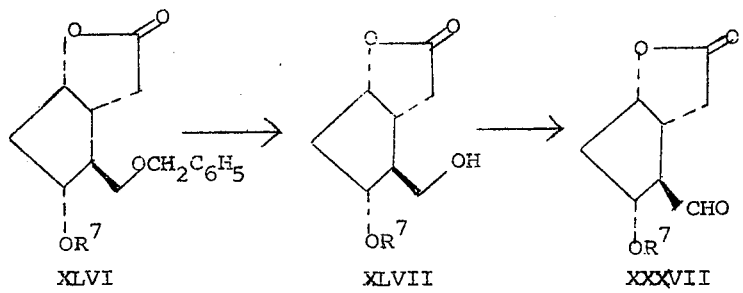

Compounds of general formula XLVII may be prepared from compounds of general formula XLVI by catalytic reduction in the presence of a hydrogenation catalyst, for example palladium on charcoal or palladium black, and converted to compounds of general formula XXXVII by oxidation under mild conditions, e.g. with Collins' reagent and at a moderately low temperature.

Compounds of general formula XXXVII may be transformed stereospecifically to trans-$\alpha,\beta$-unsaturated esters of general formula XXXVIII by reaction with the sodio derivative of compounds of general formula:

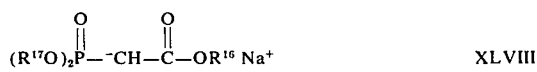

(wherein $R^{16}$ is as hereinbefore defined, and $R^{17}$ represents an alkyl group containing from 1 to 4 carbon atoms) in an inert organic solvent, e.g. tetrahydrofuran or 1,2-dimethoxyethane, at a temperature of 0°C. to 30°C. for 2 hours, in a high yield, e.g. 70% to 90%.

Compounds of general formula XXXVIII may be converted quantitatively to compounds of general formula XXXIX by reduction with more than three molar equivalents of diisobutylaluminium hydride in an inert solvent, e.g. toluene, n-pentane or n-hexane, at a low temperature, e.g. −78°C. to −20°C.

Compounds of general formula XL may be prepared by the reaction of a compound of general formula XXXIX with a compound of formula:

$$(C_6H_5)_3PCH_2{}^+CH_2CH_2CH_2COOH\cdot Br^- \qquad XLIX$$

in the presence of a strong base, for example sodiomethylsulphinyl carbanide, under the normal conditions utilized for effecting the Wittig reaction, e.g. in an inert solvent at ambient temperature. The reaction is preferably carried out in dimethyl sulphoxide because the compound of general formula XLIX is practically insoluble in other solvents, e.g. tetrahydrofuran, and because a cis-double bond must be formed stereospecifically in the Wittig reaction. For the better performance of the Wittig reaction, more than three equivalents of the phosphorane compound, prepared from the compound of general formula XLIX, are required. Reaction between the compounds of general formula XLIX and the phosphorane is usually completed in about one to five hours at laboratory temperature. The product of formula XL, i.e. the acid component of the reaction mixture, may be isolated from the reaction mixture in a high yield by conventional procedures.

Compounds of general formula XL may be esterified to obtain compounds of general formula XLI by reaction with (a) appropriate diazoalkane compounds, e.g. diazomethane, (b) appropriate alcohols in the presence of dicyclohexyl carbodiimide as condensing agent, or (c) appropriate alcohols following the formation of a mixed acid anhydride by adding a tertiary amine and then a pivaloyl halide or an arylsulphonyl or alkylsulphonyl halide (cf. our British Patents Nos. 1362956 and 1364125), and then, if desired, converted to compounds of general formula XLIII by reaction with trimethylchlorosilane in an inert organic solvent, for example methylene chloride, in the presence of a base, for example pyridine or a tertiary amine, at a low temperature, e.g. at a temperature of −30°C. to 0°C., then reacting the resulting trimethylsilyl ether with the appropriate acyl halide or acid anhydride in an inert organic solvent, for example methylene chloride, in the presence of a base, for example pyridine or a tertiary amine, at a low temperature, e.g. at a temperature of 0°C. to 30°C., and treating the resulting acyl ether by methods known per se for the removal of the trimethylsilyl group, for example by treatment with an acid; it is preferable not to use a strong acid in order to avoid the risk of the removal of the group $R^7$.

Compounds of general formula XLIII may be converted to compounds of general formula XXXVa by oxidation with manganese dioxide, for example in an inert solvent, e.g. methylene chloride, at laboratory temperature, which oxidizes an allylic alcohol group selectively.

Compounds of general formula XXXVa can be prepared from compounds of general formula XLI by oxidation with manganese dioxide, for example in an inert organic solvent, e.g. methylene chloride, at laboratory temperature, and then acylation via compounds of general formula XLII.

Compounds of general formula XXXVIII can also be prepared from compounds of general formula XLIV by selective deacetylation with an equimolar amount of anhydrous potassium carbonate in absolute methanol and then etherification with a dihydropyran, dihydrofuran or ethyl vinyl ether in an inert organic solvent, such as methylene chloride, in the presence of a condensing agent, for example p-toluenesulphonic acid.

Compounds of general formula XLVI may be prepared by known methods, for example as described in J. Org. Chem., 37, 2921 (1972) for the preparation of the compound of general formula XLVI wherein $R^7$ is a 2-tetrahydropyranyl group.

Compounds of general formula XXXV wherein X and Y represent ethylene may be obtained by reduction of compounds of general formula XXXV wherein X and Y represent vinylene by means of diimide, which is prepared from hydrazine and an oxidizing agent, for example hydroperoxide (cf. J. Chem. Ed. 42, 254 (1965). Compounds of general formula XXXV wherein X represents cis-vinylene and Y represents ethylene may be obtained by the selective reduction of the carbonyl conjugated double bond Y of compounds of general formula XXXV wherein X represents cis-vinylene and Y represents trans-vinylene by methods known per se, for example by means of lithium 1-pentyne-hydrocuprate ($LiCuH\text{-}CCC_3H_7$).

The organo-metallic compounds of general formula XXXVI may be prepared by reacting an alkyllithium compound $R^{18}$ Li (wherein $R^{18}$ represents a primary, secondary or tertiary alkyl group) with a compound of the general formula:

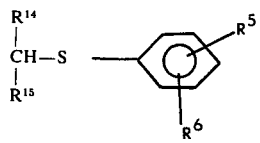

L (wherein $R^5$, $R^6$, $R^{14}$ and $R^{15}$ are as hereinbefore defined), and if desired replacing the lithium atom in the resulting compound of the general formula:

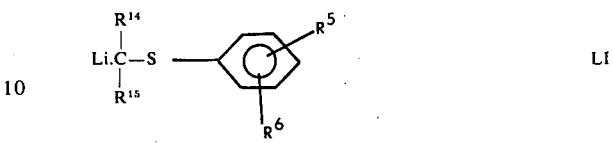

LI (wherein the various symbols are as hereinbefore defined) by a halogen atom, and reacting the haloalkyl phenyl sulphide so obtained of the general formula:

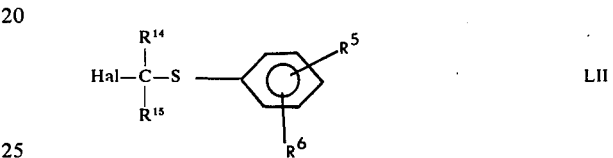

LII (wherein Hal represents a halogen atom and $R^5$, $R^6$, $R^{14}$ and $R^{15}$ are as hereinbefore defined) with magnesium to give a compound of general formula XXXVI wherein Met represents a magnesium halide group.

Compounds of general formula L and LII can be prepared by methods known per se. Suitable known compounds of formula L are p-methylphenyl methyl sulphide, m-bromophenyl methyl sulphide, m-iodophenyl methyl sulphide and p-chlorophenyl methyl sulphide.

Compounds of general formula IX, wherein X, Y, Z, $R^1$, $R^2$ and $R^7$ are as hereinbefore defined, and $R^8$ represents a 2-tetrahydropyranyl group unsubstituted or substituted by at least one alkyl group, or a 2-tetrahydrofuranyl or 1-ethoxyethyl group, may be prepared by reducing by methods known per se for the conversion of a carboxylic ester group to a formyl group, a compound of the general formula:

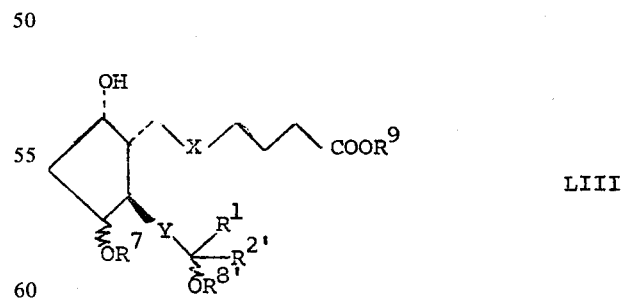

LIII (wherein X, Y, $R^1$, $R^{2'}$, $R^7$ and $R^9$ are as hereinbefore defined and $R^8$ represents a 2-tetrahydropyranyl group unsubstituted or substituted by at least one alkyl group, or a 2-tetrahydrofuranyl or 1-ethoxyethyl group) to obtain a compound of the general formula:

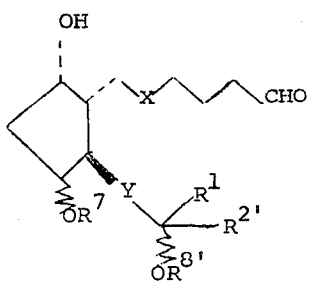

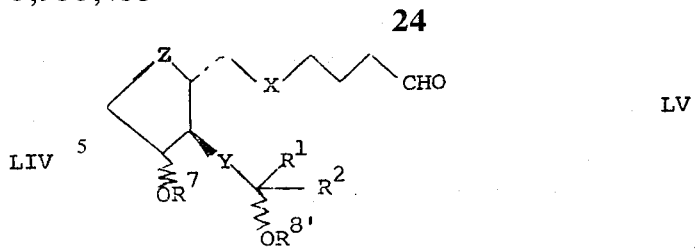

wherein Z, X, Y, $R^1$, $R^2$, $R^7$ and $R^{8'}$ are as hereinbefore defined.

Compounds of general formula LIV may also be obtained from the compounds of general formula X by etherification with a dihydropyran, dihydrofuran or ethyl vinyl ether in an inert organic solvent, such as methylene chloride, in the presence of a condensing agent, for example p-toluenesulphonic acid and then reduction by methods known per se for the conversion of a carboxylic ester to a formyl group with concomitant conversion of -$OR^{10}$ to hydroxy.

The compounds of general formula LV, which are new compounds and as such constitute a feature of the invention, may thus be converted into prostaglandin analogues of general formula VI by the reactions depicted schematically below:

(wherein X, Y, $R^1$, $R^{2'}$, $R^7$ and $R^8$ are as hereinbefore defined), optionally converting by methods known per se the 9α-hydroxy group of the compound of general formula LIV to an oxo group, or when $R^2$ represents a grouping of general formula XI wherein $R^3$, $R^5$ and $R^6$ are as hereinbefore defined and $R^{11}$ represents a sulphur atom, converting the sulphide group in the compound of general formula LIV to a sulphinyl group by oxidation by means of sodium periodate, to obtain a compound of the general formula:

CHART G

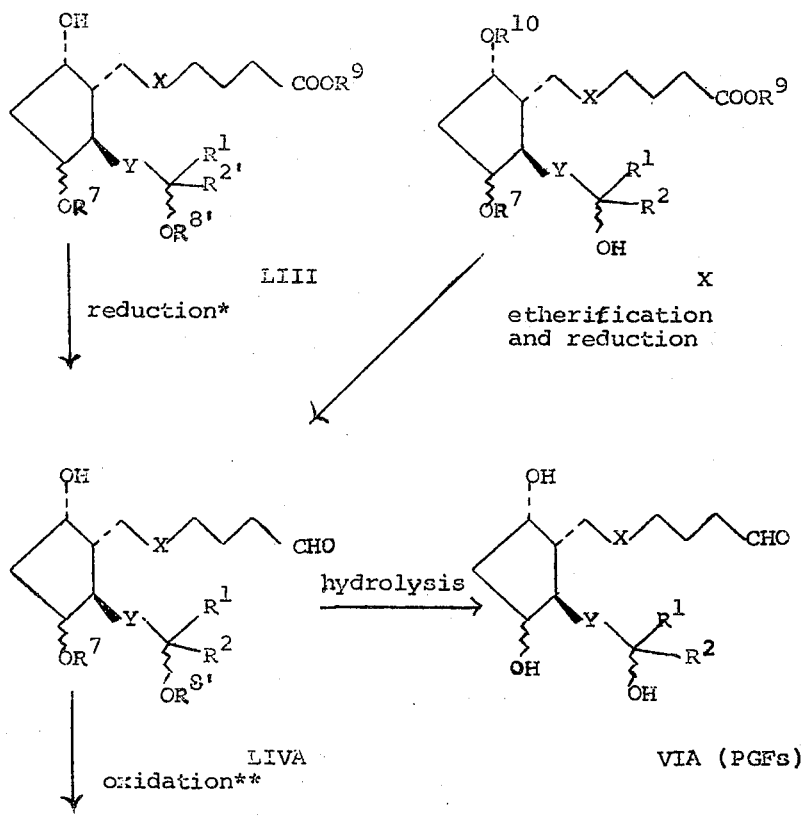

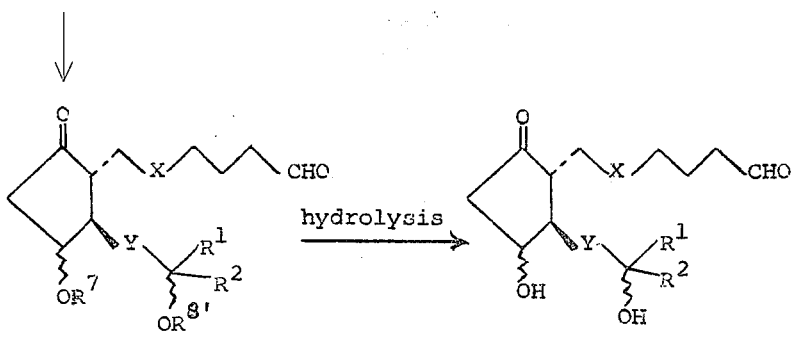

LVA                                       VIB (PGEs)

* and, when $R^{2'}$ represents a grouping of general formula XI wherein $R^3$, $R^5$ and $R^6$ are as hereinbefore defined and $R^{11}$ is a sulphur atom optional oxidation to sulphinyl
** and, when $R^2$ represents a grouping of general formula VIII wherein $R^3$, $R^5$ and $R^6$ are as hereinbefore defined and $R^4$ is a sulphur atom, optional oxidation to sulphinyl (wherein the various symbols are as hereinbefore defined.)

The groups $-OR^7$ and $-OR^{8'}$ in the intermediate compounds of general formulae LIV and LV (including LVA) may be converted into hydroxy groups using the conditions hereinbefore described for the hydrolysis of the groups $—OR^7$ and $-OR^8$ of the compounds of general formula IX.

Compounds of general formula LIVA may be converted into compounds of general formula LVA by methods known per se for the conversion of a hydroxy group in the 9-position of a prostaglandin to an oxo group, more particularly by means of an oxidizing agent which can be used under mild neutral conditions, for example by means of Collins' reagent (chromium trioxide-dipyridine complex) in an inert organic solvent, e.g. methylene cloride, below laboratory temperature for a short period of time.

Compounds of general formula LV wherein $R^2$ represents a grouping of general formula VIII wherein $R^3$, $R^5$ and $R^6$ are as hereinbefore and $R^4$ represents a sulphur atom may be oxidised, for example by means of sodium periodate, to corresponding compounds of general formula LV wherein $R^4$ in the grouping of general formula VIII represents the sulphinyl group. Oxidation with sodium periodate may be effected, for example, in a mixture of water and a lower alkanol at 0°C. for some hours, e.g., 12 hours.

The reduction of compounds of general formula LIII to compounds of general formula LIV is preferably effected according to the method of I.M. Khorlina (Tetrahedron Letters, No. 14, pp 619–620, 1962), e.g. by treating the compounds of general formula LIII with 2 to 8 molecular equivalents of diisobutylaluminium hydride in an inert organic solvent, e.g. toluene, at a temperature below −50°C. In order to prevent excessive reduction of the aldehyde product of formula LIV to the corresponding alcohol, the reduction should be terminated as rapidly as possible after the disappearance of the starting material of formula LIII. The disappearance of the starting material may be monitored by thin layer chromatography. Usually, the reduction to the desired aldehyde product is complete within 30 minutes.

Compounds of general formula LIII wherein the various symbols are as hereinbefore defined may be prepared from compounds of general formula X by etherification with a dihydropyran, dihydrofuran or ethyl vinyl ether in an inert organic solvent, such as methylene chloride, in the presence of a condensing agent, for example p-toluenesulphonic acid, with concomitant conversion of the group $-OR^{10}$ to hydroxy.

Compounds of general formula LIII wherein X, Y, $R^1$, $R^7$, $R^{8'}$ and $R^9$ are as hereinbefore defined and $R^{2'}$ represents a straight- or branched-chain alkyl group containing from 1 to 10 carbon atoms, or a straight- or branched-chain alkylene group containing from 1 to 4 carbon atoms substituted by a phenyl group or a cycloalkyl group containing from 5 to 7 carbon atoms may be prepared from compounds of the general formula:

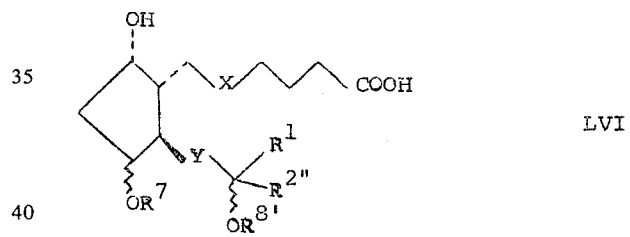

LVI (wherein X, Y, $R^1$, $R^7$ and $R^{8'}$ are as hereinbefore defined, and $R^{2''}$ represents a straight- or branched-chain alkyl group containing from 1 to 10 carbon atoms, or a straight-or branched-chain alkylene group containing from 1 to 4 carbon atoms substituted by a phenyl group or a cycloalkyl group containing from 5 to 7 carbon atoms) by the methods hereinbefore described for the conversion of compounds of general formula XL to compounds of general formula XLI.

Compounds of general formula LVI may be prepared by reacting a bicyclo-octane derivative of the general formula:

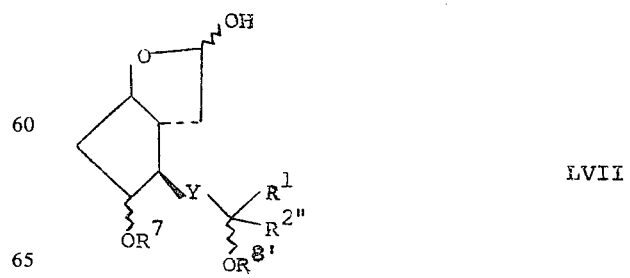

LVII (wherein Y, $R^1$, $R^7$, $R^{8'}$ and $R^{2''}$ are as hereinbefore defined) with 4-carboxy-n-butylidenetriphenyl-phosphorane to obtain a cyclopentane derivative of the general formula:

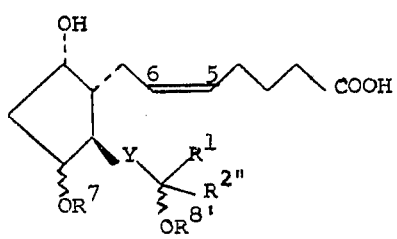

LVIII (wherein $R^1, R^7, R^{8'}, R^{2''}$ and Y are as hereinbefore defined), and optionally hydrogenating by methods known per se the cis double bond in the $C_5$-$C_6$ position to obtain a corresponding compound of the general formula:

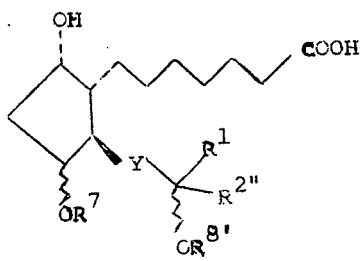

LIX wherein $R^1, R^7, R^{8'}, R^{2''}$ and Y are as hereinbefore defined.

If in general formulae LVIII and LIX Y represents a trans-vinylene group mild reducing conditions should be used for the said optional reduction step in order to reduce only the $C_5$-$C_6$ double bond and not to affect the double bond in Y. Suitably the reduction may be effected by hydrogenation in the presence of a hydrogenation catalyst, for example palladium on charcoal, in the presence of an inert organic solvent, for example a lower alkanol, e.g methanol or ethanol, at laboratory temperature at normal or elevated pressure, e.g. at a hydrogen pressure from atmospheric to 15 kilograms per square centimeter. Advantageously the quantity of hydrogen which reacts is observed during the course of the reaction so that the reaction may be terminated before any reduction of Y from trans-vinylene to ethylene occurs.

If in general formula LIX Y represents an ethylene group (Y representing in general formula LVIII either trans-vinylene or ethylene), then in the said optional reduction step more rigorous reducing conditions may be used, especially if in general formula LVIII Y represents trans-vinylene, for example hydrogenation in the presence of a hydrogenation catalyst usually used for the hydrogenation of double bonds such as various forms of platinum, palladium or nickel, in a suitable solvent (for example methanol, ethanol, water, dioxan or acetic acid or a mixture of two or more of them), at 0° to 50°C. and at normal or elevated pressure, e.g. at a hydrogen pressure from atmospheric to 15 kilograms per square centimeter.

The reaction between the bicyclo-octanes of general formula LVII and 4-carboxy-n-butylidenetriphenyl-phosphorane [obtained by the reaction of sodiomethyl-sulphinylcarbanide with 4-carboxy-n-butyltriphenyl-phosphonium bromide] is carried out under the normal conditions utilized for effecting the Wittig reaction, e.g. in an inert solvent at ambient temperature. The reaction is preferably carried out in dimethylsulphoxide because the phosphorane compound is practically insoluble in other solvents, e.g. tetrahydrofuran, and because a cis-double bond must be formed stereospecifically in the Wittig reaction. For the better performance of the Wittig reaction more than two molecular equivalents of the phosphorane compound are required for each mole of the bicyclo-octane reactant. The reaction is generally effected at a temperature of 10°–40°C., preferably at 20°–30°C., and is usually complete after about 30 minutes to four hours at laboratory temperature. The acid product of formula LVIII may be extracted from the reaction mixture by conventional procedures and further purified by column chromatography on silica gel.

The bicyclo-octane starting materials of general formula LVII wherein Y represents ethylene can be prepared by the series of reactions depicted schematically below:

CHART H

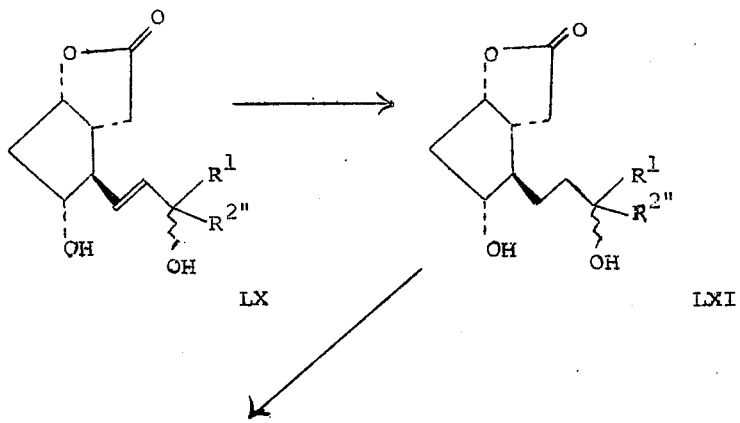

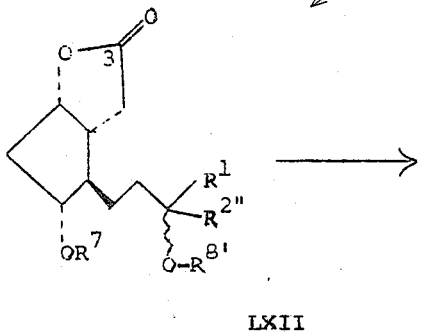

LXII

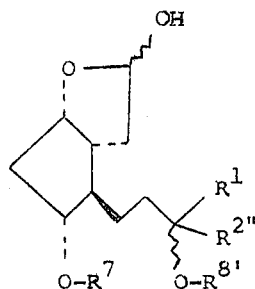

LXIII wherein $R^1$, $R^{2''}$, $R^7$ and $R^{8'}$ are as hereinbefore defined.

The compounds of formula LX are dissolved in a suitable solvent, e.g. methanol or ethanol, and then subjected to catalytic hydrogenation in the presence of a catalyst effective for the reduction of the double bond to ethylene, for example palladium on charcoal, palladium black or platinum dioxide. The resulting compounds of formula LXI are then reacted with a dihydropyran, dihydrofuran or ethyl vinyl ether in an inert organic solvent, such as methylene cloride, in the presence of a condensing agent, for example p-toluenesulphonic acid, to obtain the compounds of formula LXII. Those compounds are then reduced at a low temperature, preferably below −50°C., with a reagent capable of reducing the oxo radical in the position indicated as 3 to a hydroxy radical, preferably using diisobutylaluminium hydride.

Compounds of general formula LIII wherein X represents cis-vinylene and $R^{2'}$ represents a grouping of general formula XI wherein $R^3$, $R^5$, $R^6$ and $R^{11}$ are as hereinbefore defined may also be prepared from compounds of the general formula:

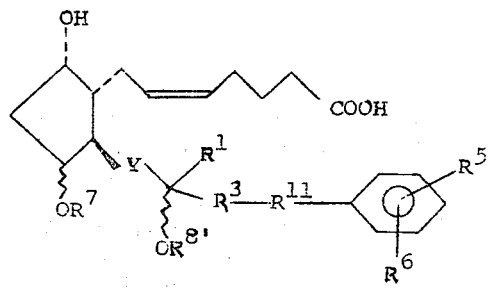

LXIV (wherein Y, $R^1$, $R^3$, $R^5$, $R^6$, $R^7$, $R^{8'}$ and $R^{11}$ are as hereinbefore defined) by the methods hereinbefore described for conversion of compounds of general formula XL to compounds of general formula XLI.

Compounds of general formula LXIV wherein $R^1$, $R^3$, $R^5$, $R^6$, $R^7$ and $R^{8'}$ are as hereinbefore defined and $R^{11}$ represents an oxygen atom may be converted to the corresponding compounds of general formula LIII, wherein Y, $R^1$, $R^7$ and $R^{8'}$ are as hereinbefore defined, X represents ethylene and $R^{2'}$ represents a grouping of general formula XI wherein $R^3$, $R^5$ and $R^6$ are as hereinbefore defined and $R^{11}$ represents an oxygen atom, by esterification, e.g. using the methods hereinbefore described for the conversion of compounds of formula XL to compounds of general formula XLI, and catalytic hydrogenation, e.g. using the conditions hereinbefore described for conversion of compounds of general formula LVIII to compounds of general formulae LIX.

Compounds of general formula LXIV may be prepared by reacting a bicyclo-octane derivative of the general formula:

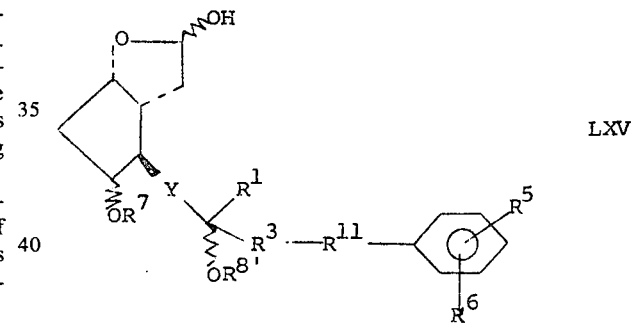

LXV (wherein Y, $R^1$, $R^3$, $R^5$, $R^6$, $R^7$, $R^{8'}$ and $R^{11}$ are as hereinbefore defined) with 4-carboxy-n-butylidenetriphenylphosphorane to obtain a cyclopentane derivative of the general formula:

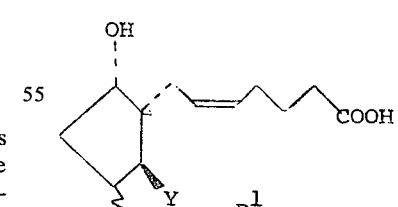

LXVI wherein $R^1$, $R^3$, $R^5$, $R^6$, $R^7$, $R^{8'}$, $R^{11}$ and Y are as hereinbefore defined.

The reaction between the bicyclo-octanes of general formula LXV and 4-carboxy-n-butylidenetriphenyl-phosphorane is carried out under the normal conditions utilized for effecting the Wittig reaction as hereinbefore described for the reaction between the bicyclo-octanes of general formula LVII and 4-carboxy-n-butylidenetriphenylphosphorane. The acid product of formula LXVI may be extracted from the reaction mixture by conventional procedures and further purified by column chromatography on silica gel.

The bicyclo-octane starting materials of general formula LXV wherein Y represents ethylene and $R^{11}$ represents an oxygen atom can be prepared by the series of reaction depicted schematically below:

The bicyclo-octane starting materials of general formula LXV wherein Y represents ethylene and $R^{11}$ represents a sulphur atom can be prepared by reduction of compounds of general formula LXV wherein Y represents trans-vinylene and $R^{11}$ represents a sulphur atom by means of diimide (NH=NH), prepared from hydrazine and an oxidizing agent, for example hydroperoxide (J. Chem. Ed. 42, 254 (1965)).

The bicyclo-octane starting materials of general formulae LVII and LXV wherein Y represents trans-vinylene and those of general formulae LX and LXVII can be prepared using initially 2-oxa-3-oxo-6-syn-formyl-7-anti-acetoxy-cis-bicyclo[3,3,0]octane (E. J. Corey et al, J. Amer. Chem. Soc. 91, 5675 (1969)) and applying thereto known procedures [see, for example J. Amer.

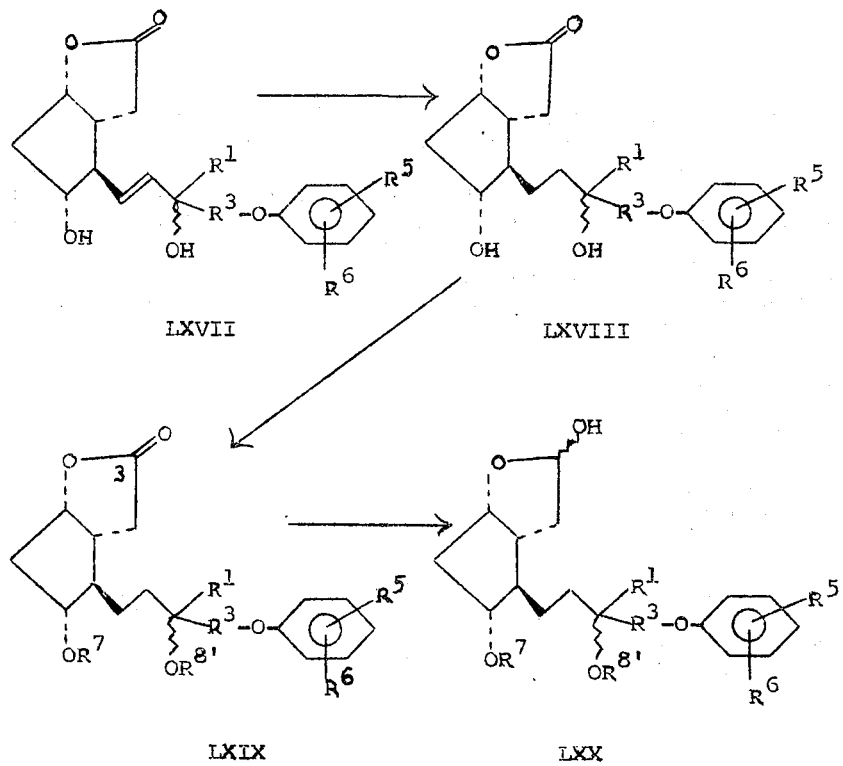

wherein $R^1$, $R^3$, $R^5$, $R^6$, $R^7$ and $R^{8'}$ are as hereinbefore defined.

The conversion of the compounds of general formula LXVII to compounds of general formula LXX via compounds of formulae LXVIII and LXIX is carried out under the conditions hereinbefore described for the conversion of compounds of formula LX to compounds of formula LXIII via compounds of formulae LXI and LXII.

The bicyclo-octane starting materials of general for-

Chem. Soc. 92, 397 (1970) and French Patent No. 7215314 (Publication No. 2134673) and German Offenlegungsschrift 2323127].

A method for the preparation of the bicyclo-octane starting materials of general formula LVII and LXV wherein Y represents trans-vinylene and the group $OR^7$ on the cyclopentane ring is in $\beta$-configuration utilizing known procedures may be represented by the series of reactions depicted schematically below (cf. Tetrahedron Letters 3265–3272, 1972):

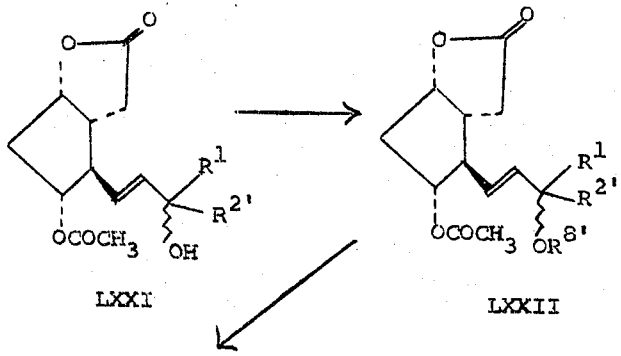

—Continued

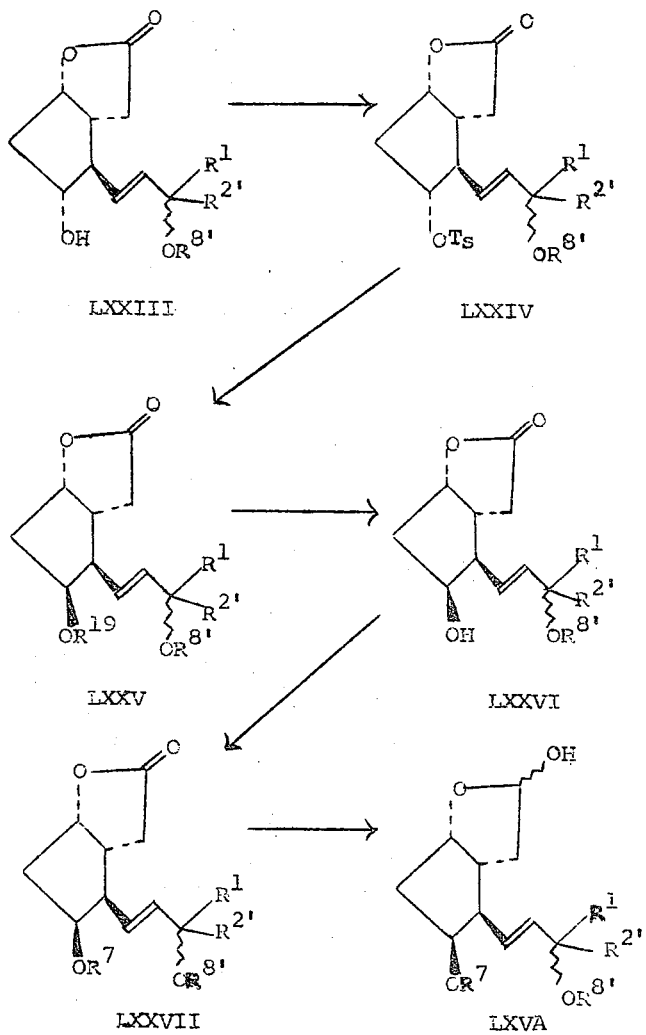

wherein $R^1$, $R^{2'}$, $R^7$ and $R^{8'}$ are as hereinbefore defined, $R^{19}$ represents the formyl group or the acetyl group (-COCH$_3$) and Ts represents the tosyl group. The various reactions depicted above may be effected by methods known per se. Compounds of general formula LXXV may be prepared by reacting compounds of general formula LXXIV with tetraethylammonium formate or tetraethylammonium acetate.

If desired, a racemic intermediate of general formula LXXI may be separated by column chromatography (c.f. Tetrahedron Letters 3269–3272, 1972) into the isomer in which the hydroxy group is in α-configuration and the isomer in which the hydroxy group is in β-configuration. These isomers of general formula LXXI may be utilized in the procedures hereinbefore described to give cyclopentane derivatives of general formula VI wherein X represents ethylene or cis-vinylene and Y represents trans-vinylene or X and Y each represent ethylene, A, $R^1$ and $R^2$ are as hereinbefore defined and the hydroxy group attached to the carbon atom adjacent to Y is in the desired α- or β-configuration. Compounds of general formula VI wherein X represents cis-vinylene and Y represents ethylene, A, $R^1$ and $R_2$ are as hereinbefore defined and the hydroxy group attached to the 11-position of the cyclopentane ring is in β-configuration may be prepared by converting a compound of general formula LXXVII (wherein $R^1$, $R^{2'}$, $R^7$ and $R^{8'}$ are as hereinbefore defined) by methods known per se for the conversion of a group $OR^7$ (wherein $R^7$ is as hereinbefore defined) into the hydroxy group, into an isomer of a compound of general formula LXVII (wherein $R^1$, $R^3$, $R^5$ and $R^6$ are as hereinbefore defined) having the hydroxy group attached to the cyclopentane ring in β-configuration, and thereafter applying the procedures hereinbefore described. Compounds of general formula VI wherein X represents cis-vinylene and Y represents ethylene, A, $R^1$ and $R^2$ are as hereinbefore defined and the hydroxy group attached to the carbon atom adjacent to Y is in the desired α- or β-configuration may be prepared by procedures hereinbefore described from intermediates of general formula LXX wherein the group represented by the symbol〜 $OR^{8'}$ is in the desired α- or β-configuration, which may themselves be prepared from the corresponding intermediates of general formula LXVII; these intermediates of general formula LXVII may be prepared, by methods known per se for the conversion of a group $OR^7$ (wherein $R^7$ is as hereinbefore defined) into the hydroxy group, from intermediate compounds of general formula LXVA prepared from the separated isomers of general formula LXXI.

By the term "methods known per se" as used in this specification is meant methods heretofore used or described in the chemical literature.

The prostaglandin compounds of general formula VI may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70°C. during the preparation of the cyclodextrin clathrates. $\alpha$, $\beta$- or $\gamma$-Cyclodextrins or mixtures thereof may be used in the preparation of the cyclodextrin clathrates. Conversion into their cyclodextrin clathrates serves to increase the stability of the prostaglandin compounds.

The prostaglandin aldehyde compounds of general formula VI may, if desired, be converted into corresponding acetals (which may be cyclic acetals) by the application or adaptation of known methods for the preparation of acetals from aldehydes, for example by the reaction of a compound of general formula VI with double the molar quantity of an alcohol or diol (for example ethanol or ethylene glycol) in the presence of an acidic catalyst, for example trifluoroborane or dry oxalic acid (cf. Synthetic Communications, 3, 125–128 (1973)). Advantageously the reaction is effected in the presence of an inert organic solvent, for example acetonitrile at room temperature. Conversion into their acetals serves to increase the stability of the aldehyde compounds.

The prostaglandin analogues of general formula VI and their cyclodextrin clathrates and acetals possess the valuable pharmacological properties typical of prostaglandins, in a selective fashion, including, in particular, hypotensive activity, abortifacient activity and stimulatory activity on uterine contraction, luteolytic activity and antinidatory activity and are useful in the treatment of hypertension, in the termination of pregnancy and induction of labour in pregnant female mammals, in the control of oestrus in female mammals and in the prevention of pregnancy in female mammals. For example, in standard laboratory screening tests, (i) by intravenous administration to the allobarbital-anaesthetized dog, 9-oxo-11$\alpha$,15$\alpha$-dihydroxy-prosta-cis-5,trans-13-dienaldehyde produces a fall in blood pressure of 16 mm.Hg lasting 6 minutes at a dose of 0.2 $\mu$g./kg. animal body weight and of 30 mm.Hg lasting 10 minutes at a dose of 0.5 $\mu$g./kg. animal body weight, 9-oxo-11$\alpha$,15$\alpha$-dihydroxy-prosta-cis-5,trans-13-dienaldehyde ethylene acetal produces a fall in blood pressure of 8 mm.Hg lasting 2 minutes at a dose of 20 $\mu$g./kg. animal body weight and of 10 mm.Hg lasting 4 minutes at a dose of 40 $\mu$g./kg. animal body weight and 16(R)-methyl-9-oxo-11$\alpha$,15$\alpha$-dihydroxy-prosta-cis-5,trans-13-dienaldehyde produces falls in blood pressure of 26 mm.Hg, 34 mm.Hg and 36 mm.Hg lasting 6 minutes, 10 minutes and 28 minutes, respectively, at doses of 0.1, 0.2 and 0.5 $\mu$g./kg. animal body weight respectively, and a fall in blood pressure of 12 mm.Hg lasting 40 minutes when administered orally to the allobarbital-anaesthetized dog at a dose of 100 $\mu$g./kg. animal body weight; (ii) 16(R)-methyl-9-oxo-11$\alpha$,15$\alpha$-dihydroxy-prosta-cis-5,trans-13-dienaldehyde and 16-(3-trifluoromethylphenoxy)-$\omega$-tetranor-9$\alpha$,11$\alpha$,15$\alpha$-trihydroxyprosta-cis-5,trans-13-dienaldehyde induce abortion in pregnant female rats when administered intraperitoneally on the 17th day of gestation at doses of 2.0 mg. and 3 to 5 $\mu$g./kg. animal body weight respectively and stimulate uterine contraction in the pregnant female rat when administered intravenously on the 20th day of gestation at a dose of 10 $\mu$g. and 2 to 5 $\mu$g./kg. animal body weight respectively; (iii) 16-(3-trifluoromethylphenoxy)-$\omega$-tetranor-9$\alpha$,11$\alpha$,15$\alpha$-trihydroxy-prosta-cis-5,trans-13-dienaldehyde inhibits implantation in pregnant female rats when administered subcutaneously on the 3rd, 4th and 5th days of pregnancy at daily doses of 5 to 10 $\mu$g./kg. animal body weight; (iv) 16(R)-methyl-9$\alpha$,11$\alpha$,15$\alpha$-trihydroxy-prosta-cis-5,trans-13-dienaldehyde and 9$\alpha$,11$\alpha$,15$\alpha$-trihydroxy-prosta-cis-5,-trans-13-dienaldehyde inhibit implantation in pregnant female rats when administered subcutaneously on the 3rd, 4th and 5th days of pregnancy at daily doses of 0.5 to 1.0 and 2.0 mg./kg. animal body weight, respectively; and (v) 9$\alpha$,11$\alpha$,15$\alpha$-trihydroxy-16-phenylthio-$\omega$-tetranor-prosta-cis-5,trans-13-dienaldehyde and 9$\alpha$,11$\alpha$,15$\alpha$-trihydroxy-16-phenoxy-$\omega$-tetranor-prosta-cis-5,trans-13-dienaldehyde induce abortion in pregnant female rats when administered intraperitoneally on the 17th day of gestation at doses of 50 $\mu$g. and 1 $\mu$g./kg. animal body weight respectively and inhibit implantation in pregnant female rats when administered subcutaneously on the 3rd, 4th and 5th days of pregnancy at daily doses of 20 $\mu$g. and 10 $\mu$g./kg. animal body weight, respectively.

Preferred prostaglandin analogues of general formula VI are those in which $R^1$ represents a hydrogen atom, and $R^2$ represents an n-pentyl group, optionally carrying a methyl substituent, or a phenoxymethyl or phenylthiomethyl group optionally substituted on the phenyl ring by a trifluoromethyl radical, and more particularly those such compounds wherein X represents cis-vinylene, and especially those in which Y represents trans-vinylene. Of outstanding importance are 16-(3-trifluoromethylphenoxy)-$\omega$-tetranor-9$\alpha$,11$\alpha$,15$\alpha$-trihydroxyprosta-cis-5,trans-13-dienaldehyde and 9$\alpha$,11$\alpha$,15$\alpha$-trihydroxy-16-phenoxy-$\omega$-tetranor-prosta-cis-5,trans-13-dienaldehyde. The following Reference Examples and Examples illustrate the process of the present invention and products thereof. In the Examples 'IR', 'NMR' and 'TLC' represent respectively 'Infrared absorption spectrum', 'Nuclear magnetic resonance spectrum' and 'Thin layer chromatography'.

REFERENCE EXAMPLE 1

Methyl 9$\alpha$-hydroxy-11$\alpha$,15$\alpha$-bis-(2-tetrahydropyranyloxy)-prosta-cis-5,trans-13-dienoate 2 g. of 9$\alpha$-hydroxy-11$\alpha$,15$\alpha$-bis(2-tetrahydropyranyloxy)-prosta-cis-5,trans-13-dienoic acid was dissolved in 70 ml. of diethyl ether and treated with a solution of freshly prepared diazomethane in diethyl ether at 0°C. until the light-yellow colour persisted and nitrogen gas was no longer evolved.

The reaction mixture was concentrated under reduced pressure and the residue was purified by column chromatography on silica gel, using a mixture of ethyl acetate - cyclohexane (1:1) as eluent, to give 1.49 g. of the title compound having the following physical characteristics:

NMR (CDCl₃ solution):δ;
5.72–5.30 (m, 4H), 4.85–4.66 (m, 2H), 4.30–3.20 (m, 11H), 3.68 (s, 3H), 1.07–0.70 (t, 3H);
TLC (developing solvent, methylene chloride - methanol = 20:1); Rf = 0.74.

EXAMPLE 1

9α-Hydroxy-11α,15α-bis-(2-tetrahydropyranyloxy)-prosta-cis-5,trans-13-dienaldehyde 1.49 g. of methyl 9α-hydroxy-11α,15α-bis(2-tetrahydropyranyloxy)-prosta-cis-5,trans-13-dienoate (prepared as described in Reference Example 1) was dissolved in 41 ml. of toluene, cooled to −60°C. and treated, dropwise with stirring, with 6.25 ml. of a 25(w/v)% solution of diisobutylaluminium hydride in toluene. The reaction mixture was stirred for a further 20 minutes at the same temperature and then methanol was added to decompose the excess of the hydride until the evolution of hydrogen ceased. The temperature was allowed to rise to 0°C. to 5°C., and then the mixture stirred for 30 minutes. The precipitate formed was filtered off and the filtrate was separated. The organic layer was washed with aqueous sodium chloride, dried over magnesium sulphate and concentrated under reduced pressure. The residue was subjected to column chromatography on silica gel, using a mixture of ethyl acetate - cyclohexane (1:3) as eluent, to give 1.30 g. of the title compound as a colourless oil having the following physical characteristics:

NMR (CDCl₃ solution):δ;
9.75 (t, 1H), 5.62–5.10 (m, 4H), 4.75–4.50 (m, 2H), 4.20–3.10 (m, 7H), 1.0–0.60 (t, 3H);
IR (liquid film):ν;
3450, 2930, 2350, 1720, 1440, 1385, 1205, 1190, 1140, 1090, 980, 820 and 740 cm⁻¹;
TLC (developing solvent, methylene chloride - methanol = 20:1); Rf = 0.60.

EXAMPLE 2

9α,11α,15α-Trihydroxy-prosta-cis-5,trans-13-dienaldehyde 300 mg. of 9α-hydroxy-11α,15α-bis-(2-tetrahydropyranyloxy)-prosta-cis-5-trans-13-dienaldehyde (prepared as described in Example 1) were dissolved in a mixture of 3.8 ml. of tetrahydrofuran, 3.37 ml. of water and 0.445 ml. of 12N hydrochloric acid and the reaction mixture stirred at room temperature for 3 hours. The reaction mixture was then treated with 0.353 g. of sodium bicarbonate and extracted with ethyl acetate. The extract was washed with water and aqueous sodium chloride, dried over magnesium sulphate and concentrated under reduced pressure. The residue was subjected to column chromatography on silica gel using a mixture of ethyl acetate - cyclohexane (3:2) as eluent to give 119 mg. of the title compound as a colourless oil having the following physical characteristics:

NMR (CDCl₃ solution):δ;
9.74 (t, 1H), 5.65–5.27 (m, 4H), 4.25–3.75 (m, 3H), 1.05–0.80 (t, 3H);
IR (liquid film):ν;
3350, 2900, 2850, 1720, 1660, 1440, 1340, 980 and 730 cm⁻¹;
TLC (developing solvent, benzene - diethyl ether - methanol = 5:2:2); Rf = 0.70.

EXAMPLE 3

9-Oxo-11α,15α-bis-(2-tetrahydropyranyloxy)-prosta-cis-5,trans-13-dienaldehyde.

63.5 ml. of methylene chloride were treated with 4.2 ml. of pyridine and then with 2.6 g. of chromium trioxide and stirred at room temperature for 15 minutes. The mixture was then treated with 11.3 g. of infusorial earth and then 1.0 g. of 9α-hydroxy-11α,15α-bis-(2-tetrahydropyranyloxy)-prosta-cis-5,trans-13-dienaldehyde (prepared as described in Example 1). The reaction mixture was stirred for 15 minutes, treated with 18 g. of sodium hydrogen sulphate monohydrate and filtered through a pad of magnesium sulphate. After washing the solids with methylene chloride the solution was concentrated under reduced pressure. The residue was subjected to column chromatography on silica gel, using a mixture of ethyl acetate - cyclohexane (1:3) as eluent to give 0.7 g. of the title compound as a colourless oil having the following physical characteristics:

NMR (CDCl₃ solution):δ;
9.75 (t, 1H), 5.80–5.00 (m, 4H), 4.80–4.50 (m, 2H), 4.30–3.20 (m, 6H), 1.00–0.70 (t, 3H);
IR (liquid film):ν;
2900, 2830, 1740, 1720, 1460, 1360, 1330, 1270, 1210, 1140, 1080, 1045, 1030, 980, 920, 880 and 825 cm⁻¹;
TLC (developing solvent, methylene chloride - methanol = 20:1); Rf = 0.86.

EXAMPLE 4

9-Oxo-11α,15α-dihydroxy-prosta-cis-5,trans-13-dienaldehyde 500 mg. of 9-oxo-11α,15α-bis-(2-tetrahydropyranyloxy)-prosta-cis-5,trans-13-dienaldehyde (prepared as described in Example 3) were dissolved in 15 ml. of a mixture of acetic acid, water and tetrahydrofuran (65:35:10) and the reaction mixture was stirred at 38°C. for 4 hours. It was poured into 35 ml. of ice-water and extracted with ethyl acetate. Drying, evaporation of the solvent under reduced pressure, and purification of the product by column chromatography on silica gel using a mixture of ethyl acetate - cyclohexane (1:3) as eluent gave 138 mg. of the title compound as a colourless oil having the following physical characteristics:

NMR (CDCl$_3$ solution):δ;
  9.50 (t, 1H), 5.70–5.48 (m, 2H), 5.48–5.25 (m, 2H), 4.22–3.90 (m, 2H), 1.05–0.75 (t, 3H);
IR (liquid film)ν;

3400, 2930, 2850, 1740, 1450, 1405, 1320, 1245, 1160, 1080, 975 and 730 cm$^{-1}$;
TLC (developing solvent, chloroform - tetrahydrofuran - acetic acid = 10:2:1); Rf = 0.50.

REFERENCE EXAMPLE 2

Methyl 16(R)-methyl-9α-hydroxy-11α,15αbis-(2-tetrahydropyranyloxy)-prosta-cis-5,trans-13-dienoate 3.0 g. of 16(R)-methyl-9α-hydroxy-11α,15α-bis-(2-tetrahydropyranyloxy)-prosta-cis-5,trans-13-dienoic acid [prepared as described in Example 1 of French Patent Application No. 72.15314 (Publication No. 2134673)] were dissolved in 80 ml. of diethyl ether and treated with a solution of freshly prepared diazomethane in diethyl ether at 0°C. until the light-yellow colour persisted and nitrogen gas was no longer evolved. The reaction mixture was concentrated under reduced pressure and the residue was purified by column chromatography on silica gel using a mixture of ethyl acetatecyclohexane (1:1) as eluent to give 2.26 g. of the title compound having the following physical characteristics:

NMR (CDCl$_3$ solution):δ;
  5.72–5.27 (m, 4H), 4.86–4.65 (m, 2H), 3.68 (s, 3H), 1.07–0.72 (m, 6H);
TLC (developing solvent, methylene chloride - methanol = 20:1) Rf = 0.75.

EXAMPLE 5

16(R)-Methyl-9α-hydroxy-11α,15α-bis-(2-tetrahydropyranyloxy)-prosta-cis-5,trans-13-dienaldehyde 2.09 g. of methyl 16(R)-methyl-9α-hydroxy-11α,15α-bis-(2-tetrahydropyranyloxy)-prosta-cis-5,-trans-13-dienoate (prepared as described in Reference Example 2) were dissolved in 50 ml. of toluene, cooled to −70°C. and treated, dropwise with stirring, with 8.25 ml. of a 25(w/v)% solution of diisobutylaluminium hydride in toluene. The reaction mixture was stirred for 15 minutes at the same temperature and then methanol was added to decompose the excess of the hydride until the evolution of hydrogen ceased. The temperature was allowed to rise to 0°C. to 5°C. and about 15 ml. of water were added to the reaction mixture whilst maintaining the temperature below 30°C. The precipitate formed was filtered off and the filtrate was separated into layers. The organic layer was washed with aqueous sodium chloride, dried over magnesium sulphate and concentrated under reduced pressure to give 1.97 g. of the title compound as an oil having the following physical characteristics:

NMR (CDCl$_3$ solution):δ;
  9.75 (t, 1H), 5.62–5.10 (m, 4H), 4.75–4.50 (m, 2H), 4.20–3.10 (m, 8H), 1.0–0.60 (m, 6H);

IR (liquid film):ν;
  3450, 2930, 2720, 1725, 1660, 1460, 1440, 1380, 1350, 1205, 1185, 1140, 1080, 980, 820 and 740 cm$^{-1}$;

TLC (developing solvent, methylene chloride - methanol = 20:1); Rf = 0.40.

EXAMPLE 6

16(R)-Methyl-9α,11α,15α-trihydroxy-prosta-cis-5,trans-13-dienaldehyde 570 mg. of 16(R)-methyl-9α-hydroxy-11α,15α-bis-(2-tetrahydropyranyloxy)-prosta-cis-5,trans-13-dienaldehyde (prepared as described in Example 5) were dissolved in a mixture of 5.0 ml. of tetrahydrofuran, 4.16 ml. of water and 0.55 ml. of 12N hydrochloric acid and the reaction mixture stirred at 35°C. to 40°C. for one hour. The reaction mixture was then treated with 0.436 g. of sodium bicarbonate and extracted with ethyl acetate. The extract was washed with water and aqueous sodium chloride, dried over magnesium sulphate and concentrated under reduced pressure. The residue was subjected to column chromatography on silica gel using a mixture of ethyl acetate - cyclohexane (2:1) as eluent to give 205 mg. of the title compound as a colourless oil having the following physical characteristics:

NMR (CDCl$_3$ solution);δ;
  9.74 (t, 1H), 5.65–5.27 (m, 4H), 4.25–3.75 (m, 3H), 2.65 (broad s, 3H), 2.44 (d-t, 2H), 0.95 (d, 3H), 0.90 (t, 3H);

IR (liquid film):ν;
  3350, 2920, 2860, 2720, 1725, 1660, 1460, 1440, 1380, 1340, 980 and 760 cm$^{-1}$;

TLC (developing solvent, chloroform - tetrahydrofuran - acetic acid = 10:2:1); Rf = 0.21.

EXAMPLE 7

16(R)-Methyl-9-oxo-11α,15α-bis-(2-tetrahydropyranyloxy)-prosta-cis-5,trans-13-dienaldehyde 62 ml. of methylene chloride were treated with 4.08 ml. of pyridine and then 2.52 g. of chromium trioxide and stirred at room temperature for 15 minutes. The reaction mixture was then treated with 11 g. of infusorial earth and then 1.0 g. of 16(R)-methyl-9α-hydroxy-11α,15α-bis-(2-tetrahydropyranyloxy)-prosta-cis-5,trans-13-dienaldehyde (prepared as described in Example 5) was added. The reaction mixture was stirred for 15 minutes, treated with 18 g. of sodium hydrogen sulphate monohydrate and filtered through a pad of magnesium sulphate. After washing the solids with methylene chloride, the solution was concentrated under reduced pressure to about 5 ml., diluted with diethyl ether and washed with an aqueous solution of oxalic acid. The aqueous layer was extracted with diethyl ether, and the ethereal layer was washed with water and aqueous sodium chloride, dried over magnesium sulphate and concentrated under reduced pressure. The residue was subjected to column chromatography on silica gel using a mixture of ethyl acetate - cyclohexane (1:4) as eluent to give 0.580 g. of the title compound as a colourless oil having the following physical characteristics:

NMR (CDCl$_3$ solution):δ;
  10.0 (t, 1H), 5.85–5.10 (m, 4H), 4.90–4.55 (m, 2H), 4.40–3.20 (m, 6H), 1.02 (d, 3H), 0.925 (t, 3H);

IR (liquid film):ν;
  2960, 2925, 2870, 2850, 2720, 1745, 1725, 1460, 1410, 1380, 1330, 1270, 1210, 1140, 1080, 1045, 1030, 980, 920, 880 and 825 cm$^{-1}$;

TLC (developing solvent, ethyl acetate - benzene = 1:2); Rf = 0.67.

EXAMPLE 8

16(R)-Methyl-9-oxo-11α,15α-dihydroxy-prosta-cis-5,-trans-13-dienaldehyde 580 mg. of 16(R)-methyl-9-oxo-11α,15α-bis-(2-tetrahydropyranyloxy)-prosta-cis-5,trans-13-dienaldehyde (prepared as described in Example 7) were dissolved in 16.5 ml. of a mixture of acetic acid, water and tetrahydrofuran (65:35:10) and the reaction mixture was stirred at 38°C. for 4 hours. Then the reaction mixture was poured into 35 ml. of ice-water and extracted with ethyl acetate. Drying, evaporation of the solvent under reduced pressure and purification of the product by column chromatography on silica gel using a mixture of ethyl acetate and cyclohexane (1:1) as eluent gave 163 mg. of the title compound as a colourless oil having the following physical characteristics:

NMR (CDCl$_3$ solution);δ;
  9.75 (t, 1H), 5.70–5.50 (m, 2H), 5.50–5.25 (m, 2H), 4.22–3.75 (m, 2H), 2.43 (t-d, 2H), 1.05–0.75 (m, 6H);

IR (liquid film):ν;
  3400, 2960, 2925, 2870, 2850, 2720, 1745, 1725, 1460, 1410, 1380, 1250, 1160, 1080, 975 and 730 cm$^{-1}$;

TLC (developing solvent, chloroform - tetrahydrofuran - acetic acid = 10:2:1); Rf = 0.41.

EXAMPLE 9

9-Oxo-11α,15α-dihydroxy-prosta-cis-5,trans-13-dienaldehyde ethylene acetal

Under an atmosphere of nitrogen, 200 mg. of 9-oxo-11α,15α-dihydroxy-prosta-cis-5,trans-13-dienaldehyde (prepared as described in Example 4) were dissolved in dry acetonitrile and 37 mg. of ethylene glycol and 53.6 mg. of dry oxalic acid were added to the solution and stirred at room temperature for one hour. Then water was added to the mixture, which was extracted with a mixture of n-hexane and diethyl ether (1:1). The extract was washed with water and aqueous sodium chloride, dried over magnesium sulphate and concentrated under reduced pressure. The residue was subjected to column chromatography on silica gel using methylene chloride as eluent to give 145 mg. of the title compound as a colourless oil which solidified on standing; the solid melted at 50.5 to 53.0°C. and had the following physical characteristics:

NMR (CDCl$_3$ solution):δ;
  5.77–5.20 (m, 4H), 4.90–4.76 (t, 1H), 4.26–3.59 (m, 8H);

IR (KBr tablet):ν;
  3500, 3330, 2940, 2860, 1740, 1462, 1440, 1415, 1385, 1322 and 1255 cm$^{-1}$;

TLC (developing solvent, methylene chloride - methanol = 20:1); Rf = 0.31.

REFERENCE EXAMPLE 3

2-Oxa-3-oxo-6-syn-(2-methoxycarbonyl-eth-trans-1-enyl)-7-anti-acetoxy-cis-bicyclo[3,3,0]octane Under an atmosphere of nitrogen and at laboratory temperature, 140, ml. of absolute methylene chloride and 16.1 ml. of absolute pyridine were stirred with 10 g. of chromium trioxide for 30 minutes. 20 g. of infusorial earth were then added to the solution. After cooling the temperature to 0°C., 2.14 g. of 2-oxa-3-oxo-6-syn-hydroxymethyl-7-anti-acetoxy-cis-bicyclo[3,3,-0]octane [prepared as described in J. Amer. Chem. Soc., 92,397 (1970)] in 20 ml. of methylene chloride were then added and the mixture stirred for 15 minutes at 0°C. The reaction mixture was then treated with 25 g. of sodium bisulphate and stirred for a further 10 minutes at 0°C. and filtered through a pad of magnesium sulphate. The filtrate was then concentrated under reduced pressure and below 0°C. to give 2-oxa-3-oxo-6-syn-formyl-7-anti-acetoxy-cis-bicyclo[3,3,0]octane.

369 mg. of sodium hydride (65% content) were suspended in 60 ml. of absolute tetrahydrofuran. With stirring under an atmosphere of nitrogen at room temperature, 1.82 g. of trimethyl phosphonoacetate [prepared as described in Acad. Sci. Paris. Ser. A,B 262B,515 (1966)] were added to the suspension, and stirred for 30 minutes.

The formyl compound, obtained above, in 30 ml. of tetrahydrofuran, was added, whilst maintaining the temperature below 15°C., and stirred for 2 hours at 15°C. Then the reaction mixture was treated with 2 ml. of acetic acid to pH 5 and concentrated slightly. The product was treated with 20 ml. of water and extracted twice with 80 ml. of ethyl acetate (total volume 160 ml.). The organic layer was washed with an aqueous solution of sodium chloride, dried over magnesium sulphate and concentrated under reduced pressure. The residue was purified by column chromatography on silica gel using a mixture of ethyl acetate - benzene (1:4) as eluent to give 2.0 g. of the title compound having the following physical characteristics:
IR (liquid film);$\nu$:
  2970, 1775, 1735, 1710, 1650, 1240, 1160, 1037, and 980 $cm^{-1}$;
NMR ($CDCl_3$ solution);$\delta$:
  6.77 (1H, d), 5.87 (1H, d), 5.00 (2H, m), 3.70 (3H, s), 3.0–1.9 (6H, m), 2.04 (3H, s);
TLC (developing solvent, ethyl acetate - benzene = 1:2); Rf = 0.38.

REFERENCE EXAMPLE 4

2-Oxa-3-oxo-6-syn-(2-methoxycarbonyl-eth-trans-1-enyl)-7-anti-hydroxy-cis-bicyclo[3,3,0]octane.

2.68 g. of 2-oxa-3-oxo-6-syn-(2-methoxycarbonyleth-trans-1-enyl)-7-anti-acetoxy-cis-bicyclo[3,3,-0]octane (prepared as described in Reference Example 3) in 30 ml. of absolute methanol and 1.38 g. of potassium carbonate were stirred at room temperature for 15 minutes, successively cooled in an ice-bath and neutralized with 20 ml. of 1N hydrochloric acid. 260 ml. of ethyl acetate and 27 ml. of an aqueous solution of sodium bicarbonate were added to the reaction mixture and separated into two layers. The organic layer was washed with an aqueous solution of sodium chloride, dried over magnesium sulphate and concentrated under reduced pressure to give 1.96 g. of the title compound having the following physical characteristics:
IR (liquid film);$\nu$:
  3430, 1786–1690 (broad) and 1650 $cm^{-1}$;
NMR ($CDCl_3$ solution);$\delta$:
  6.82 (1H, dd), 5.90 (1H, d), 4.95 (1H, m), 3.72 (3H, s), 4.30 – 3.25 (2H, m) and 2.90–1.70 (6H, m);
TLC (developing solvent, methylene chloride - methanol = 19:1); Rf = 0.38.

REFERENCE EXAMPLE 5

2-Oxa-3-oxo-6-syn-(2-methoxycarbonyl-eth-trans-1-enyl)-7-anti-(2-tetrahydropyranyloxy)-cis-bicyclo[3,3,0]octane 2.31 g. of 2-oxo-6-syn-(2-methoxycarbonyleth-trans-1-enyl)-7-anti-hydroxy-cis-bicyclo[3,3,0]octane (prepared as described in Reference Example 4) were dissolved in 30 ml. of methylene chloride and stirred with 20 mg. of p-toluenesulphonic acid and 3 ml. of dihydropyran for 15 minutes at room temperature. The reaction mixture was neutralized with an aqueous solution of sodium bicarbonate, diluted with ethyl acetate, washed with an aqueous solution of sodium chloride, dried over magnesium sulphate and concentrated under reduced pressure. The residue was purified by column chromatography on silica gel using a mixture of ethyl acetate - benzene (1:3) as eluent to give 3.0 g. of the title compound as white crystals having the following physical characteristics: m.p. ; 85°C.;
IR (KBr tablet);$\nu$:
  2930, 1770, 1710, 1650, 1343, 1240 and 1152 $cm^{-1}$;
NMR ($CDCl_3$ solution);$\delta$;
  6.78 (1H, dd), 5.84 (1H, d), 4.97 (1H, m), 4.63 (1H, m), 3.71 (3H, s) and 4.30–3.20 (3H, m);
TLC (developing solvent, ethyl acetate - benzene = 1:2); Rf = 0.34.

REFERENCE EXAMPLE 6

2-Oxa-3-hydroxy-6-syn-(3-hydroxy-prop-trans-1-enyl)-7-anti-(2-tetrahydropyranyloxy)-cis-bicyclo[3,3,0]octane 3.10 g. of 2-oxa-3-oxo-6-syn-(2-methoxycarbonyleth-trans-1-enyl)-7-anti-(2-tetrahydropyranyloxy)-cis-bicyclo[3,3,0]octane (prepared as described in Reference Example 5) were dissolved in 100 ml. of toluene and cooled to −65°C. To the solution, 23 ml. of a 25(w/v)% solution of diisobutylaluminium hydride in toluene were added and stirred for 20 minutes at −60°C. Methanol was then added to decompose excess diisobutylaluminium hydride together with water. The precipitate was filtered off and the filtrate was dried and concentrated under reduced pressure to give 2.8 g. of the title compound having the following physical characteristics:
IR (liquid film);$\nu$;
  3390, 2930, 1350 and 1120 $cm^{-1}$;
NMR ($CDCl_3$ solution);$\delta$;
  5.75–5.15 (3H, m) and 4.75–3.34 (8H, m);
TLC (developing solvent, methylene chloride - methanol = 19:1); Rf = 0.23.

REFERENCE EXAMPLE 7

2$\alpha$-(6-Methoxycarbonyl-hex-cis-2-enyl)-3$\beta$-(3-hydroxy-prop-trans-1-enyl)-4$\alpha$-(2-tetrahydropyranyloxy)-cyclopentan-1$\alpha$-ol 2.94 g. of sodium hydride (65% content) were suspended in 40 ml. of dimethyl sulphoxide and stirred with heating at 65°C. for 40 minutes to obtain sodiomethylsulphinyl carbanide. The reaction mixture was allowed to cool to room temperature and then added dropwise to a solution of 18.5 g. of 4-hydroxycarbonyl-n-butyl-triphenylphosphonium bromide in 40 ml. of dimethyl sulphoxide, the reaction temperature being kept within the range of 20°C. to 25°C.

A solution of 2.84 g. of 2-oxa-3-hydroxy-6-syn-(3-hydroxy-prop-trans-1-enyl)-7-anti-(2-tetrahydropyranyloxy)-cis-bicyclo[3,3,0]octane (prepared as described in Reference Example 6) in 40 ml. of dimethyl sulphoxide was added, and the mixture stirred vigorously at 25°C. for 1 hour. The reaction mixture was poured into 500 ml. of ice-water and neutral substances were removed by extraction with a mixture of ethyl acetate and diethyl ether (1:1). The aqueous layer was acidified to pH 3 with a saturated solution of oxalic acid and extracted with a mixture of diethyl ether and ethyl acetate (1:1). The extracts, after washing with water, were dried over magnesium sulphate and concentrated under reduced pressure to give crude 2α-(6-hydroxycarbonyl-hex-cis-2-enyl)-3β-(3-hydroxy-prop-trans-1-enyl)-4α-(2-tetrahydropyranyloxy)-cyclopentan-1α-ol having the following physical characteristics:

IR (liquid film):ν;
  2930, 1720, 1240 and 1120 cm$^{-1}$;
NMR (CDCl$_3$ solution):δ;
  5.70–5.25 (4H, m) and 4.62 (1H, m);
TLC (developing solvent, methylene chloride - methanol = 19:1); Rf = 0.23.

The crude 6-hydroxycarbonyl compound thus obtained was dissolved in 40 ml. of methylene chloride, cooled to 0°C. and a solution of diazomethane in diethyl ether was added until the reaction mixture was coloured pale yellow. The reaction mixture was then concentrated under reduced pressure and the residue was subjected to column chromatography on silica gel using a mixture of ethyl acetate - cyclohexane (1:1) as eluent to give 2.87 g. of the title compound having the following physical characteristics:-

IR (liquid film):ν;
  3420, 2930, 1740, 1435 and 1020 cm$^{-1}$;
NMR (CDCl$_3$ solution):δ;
  5.75–5.20 (4H, m), 4.67 (1H, m), 4.20–3.30 (6H, m) and 3.67 (3H, s);
TLC (developing solvent, ethyl acetate - cyclohexane = 2:1); Rf = 0.31.

REFERENCE EXAMPLE 8

2α-(6-Methoxycarbonyl-hex-cis-2-enyl)3β-(2-formyl-eth-trans-1-enyl)-4α-(2-tetrahydropyranyloxy)-cyclopentan-1α-ol 3.8 g. of active manganese dioxide were added to a solution of 382 mg. of 2α-(6-methoxycarbonyl-hex-cis-2-enyl)- 3β-(3-hydroxy-prop-trans-1-enyl)-4α-(2-tetrahydropyranyloxy)-cyclopentan-1α-ol (prepared as described in Reference Example 7) in 30 ml. of methylene chloride, the mixture stirred at room temperature for 2 hours and filtered. The precipitate was washed thoroughly with acetone, and the filtrate and washing were combined and concentrated under reduced pressure. The residue was purified by column chromatography on silica gel using a mixture of ethyl acetate - benzene (1:4) as eluent to give 266 mg. of the title compound having the following physical characteristics:

IR (liquid film):ν;
  3450, 2930, 1737, 1688, 1632, 1435, 1125, 1022 and 977 cm$^{-1}$;
NMR (CDCl$_3$ solution):δ; 9.56 (1H, d), 6.82 and 6.79 (1H, dd, respectively), 6.20 and 6.18 (1H, dd, respectively), 5.36 (2H, m), 4.58 (1H, m), 3.61 (3H, s) and 4.30–3.20 (4H, m);
TLC (developing solvent, ethyl acetate - benzene = 1:2: Rf = 0.27.

REFERENCE EXAMPLE 9

1α-Acetoxy-2α-(6-methoxycarbonyl-hex-cis-2-enyl)-3β-(2-formyl-eth-trans-1-enyl)-4α-(2-tetrahydropyranyloxy)-cyclopentane 380 mg. of 2α-(6-methoxycarbonyl-hex-cis-2-enyl)-3β-(2-formyl-eth-trans-1-enyl)-4α-(2-tetrahydropyranyloxy)-cyclopentan-1α-ol (prepared as described in Reference Example 8) were dissolved in 1.61 ml. of pyridine and 1.87 ml. of acetic anhydride were added and stirred at room temperature for 5 hours. The reaction mixture was concentrated under reduced pressure, the residue was dissolved in 50 ml. of ethyl acetate and 5 ml. of 0.05N hydrochloric acid were added. After separation into two layers, the organic layer was washed with an aqueous solution of sodium chloride, dried over magnesium sulphate and concentrated under reduced pressure. The residue was purified by column chromatography on silica gel using a mixture of ethyl acetate - benzene (1:4) as eluent to give 380 mg. of the title compound having the following physical characteristics:

IR (liquid film):ν;
  2930, 1737, 1687, 1636, 1244, 1127 and 1030 cm$^{-1}$;
NMR (CDCl$_3$ solution):δ;
  9.56 (1H, d), 6.82 and 6.79 (1H, each dd), 6.26 and 6.23 (1H, each dd), 5.34 (2H, m), 5.11 (1H, m), 4.56 (1H, m), 4.27–3.25 (3H, m), 3.67 (3H, s), 2.09 (3H, s) and 3.00–1.26 (18H, m);
TLC (developing solvent, ethyl acetate - benzene = 1:2); Rf = 0.50.

REFERENCE EXAMPLE 10

Methyl 9α-acetoxy-11α-(2-tetrahydropyranyloxy)-15α-hydroxy-16-phenylthio-ω-tetranor-prosta-cis-5,trans-13-dienoate and its 15β-hydroxy epimer 37.5 ml. of a 1.6N n-butyl lithium solution in diethyl ether were added dropwise to a solution of 6.0 ml. of thioanisole in 60 ml. of tetrahydrofuran under an atmosphere of nitrogen at −10°C and the reaction mixture was stirred at the same temperature for one hour. The reaction mixture thus obtained was added dropwise at −60°C to a solution of 12.0 g. of 1α-acetoxy-2α-(6-methoxycarbonyl-hex-cis-2-enyl)-3β-(2-formyl-eth-trans-1-enyl)-4α-(2-tetrahydropyranyloxy)-cyclopentane (prepared as described in Reference Example 9) in 150 ml. of tetrahydrofuran and the reaction mixture was stirred at that temperature for a further 20 minutes, acidified with acetic acid, diluted with water and extracted with ethyl acetate. The organic extracts were washed with aqueous sodium bicarbonate and aqueous sodium chloride solutions, dried over magnesium sulphate and concentrated under reduced pressure. The residue was purified by column chromatography on silica gel using a mixture of cyclohexane and ethyl acetate (4:1) as eluent to give 5.2 g. of the 15α-hydroxy compound, 6.2 g. of the 15β-hydroxy compound and 3.3 g. of a mixture thereof having the following physical characteristics:

TLC (developing solvent, benzene - ethyl acetate = 2:1):
  15α-hydroxy compound: Rf = 0.31; 15β-hydroxy compound: Rf = 0.42;
IR (liquid film):ν;
  3430, 2930, 2850, 1730, 1580, 1435, 1370, 1250, 1025, 975, 920, 870 cm$^{-1}$;
NMR (CDCl$_3$ solution):δ; 7.7–7.2 (5H, m), 5.9–5.6 (2H, m), 5.6–5.3 (2H, m), 5.3–4.9 (1H, m), 4.9–4.5 (1H, m), 4.5–3.3 (5H, m), 3.73 (3H, s), 3.12 (2H, d), 2.33 (2H, t), 2.1 (3H, s).

EXAMPLE 10

9α-15α-Dihydroxy-11α-(2-tetrahydropyranyloxy)-16-phenylthio-ω-tetranor-prosta-cis-5,trans-13-dienaldehyde 500 mg. of methyl 9α-acetoxy-11α-(2-tetrahydropyranyloxy)-15α-hydroxy-16-phenylthio-ω-tetranor-prosta-cis-5,trans-13-dienoate (prepared as described in Reference Example 10) were dissolved in 12 ml. of toluene and, after cooling to −70°C, 1.14 ml. of a 25 (w/v)% solution of diisobutylaluminium hydride in toluene were added dropwise under an atmosphere of nitrogen with stirring. After subjecting the ester to reduction for 30 minutes at −60°C, the reaction mixture was treated with methanol in order to decompose the unreacted diisobutylaluminium hydride. The reaction mixture was warmed to 0° to 5°C and 15 ml. of water were added to the mixture which was then stirred for 30 minutes. The resulting precipitate was filtered off and the filtrate was separated into two layers. The organic layer was washed with an aqueous sodium chloride solution, dried over magnesium sulphate and concentrated under reduced pressure. The residue was purified by column chromatography on silica gel using a mixture of ethyl acetate and cyclohexane (1:3) as eluent to give 150 mg. of the title compound having the following physical characteristics:

TLC (developing solvent, benzene - ethyl acetate = 1:1): Rf = 0.44;
IR (liquid film):$\nu$;
  3410, 2940, 2850, 1720, 1580, 1480, 1440, 1380, 1360, 1330, 1255, 1205 cm$^{-1}$;
NMR (CDCl$_3$ solution):$\delta$;
  7.70–7.05 (5H, m), 5.90–5.20 (4H, m), 4.85–4.45 (1H, m).

EXAMPLE 11

9α,11α,15α-Trihydroxy-16-phenylthio-ω-tetranor-prosta-cis-5,trans-13dienaldehyde 150 mg. of 9α,15α-dihydroxy-11α-(2-tetrahydropyranyloxy)-16-phenylthio-ω-tetranor-prosta-cis-5,trans-13dienaldehyde (prepared as described in Example 10) were dissolved in a mixture of 1.51 ml. of tetrahydrofuran, 0.66 ml. of water and 0.089 ml. of 12N hydrochloric acid and the reaction mixture was stirred at room temperature for 1.5 hours. 69 mg. of sodium bicarbonate were added to the reaction mixture, which was then extracted with ethyl acetate. The organic extracts were washed with an aqueous sodium chloride solution, dried over magnesium sulphate and concentrated under reduced pressure. The residue was purified by column chromatography on silica gel using a mixture of ethyl acetate and cyclohexane (1:1) as eluent to give 97 mg. of the title compound having the following physical characteristics:

TLC (developing solvent, chloroform-tetrahydrofuran-acetic acid = 10:2:1): Rf = 0.32 ;
IR (liquid film):$\nu$;
  3350, 2920, 2720, 1720, 1670, 1590, 1480, 1440, 1030, 975 cm$^{-1}$;
NMR (CDCl$_3$ solution):$\delta$;
  7.48–7.06 (5H, m), 5.60–5.10 (4H, m), 4.30–3.70 (3H, m), 3.60–2.50 (5H, m).

REFERENCE EXAMPLE 11

Dimethyl 2-oxo-3-(3-trifluoromethylphenoxy)propylphosphonate 24 g. of 3-trifluoromethylphenol, 19.2 g. of ethyl chloroacetate, 22.5 g. of sodium iodide and 20.8 g. of potassium carbonate were added to 75 ml. of dry acetone and the reaction mixture was refluxed for 16 hours. Then the reaction mixture was poured into a cold aqueous hydrochloric acid solution and extracted with ethyl acetate. The organic extracts were washed with water and an aqueous sodium chloride solution, dried over magnesium sulphate and concentrated under reduced pressure. The residue was purified by distillation in vacuo to give 29.5 g. of ethyl (3-trifluoromethylphenoxy)acetate having the following physical characteristics:

boiling point: 122 to 125°C./19 mm Hg;
IR (liquid film):$\nu$;
  1750, 1590, 1330, 1130 cm$^{-1}$;
NMR (CCl$_4$ solution):$\delta$;
  7.65 - 6.90 (4H, m), 4.64 (2H, s), 4.25 (2H, q), 1.25 (3H, t).

33.0 g. of dimethyl methylphosphonate were dissolved in 260 ml. of anhydrous tetrahydrofuran, to which 131 ml. of a solution of 2N n-butyllithium in n-hexane were added dropwise whilst maintaining the temperature from −60° to −55°C. After stirring for 30 minutes, 29.5 g. of ethyl (3-trifluoromethylphenoxy)-acetate (obtained as described above) in 100 ml. of anhydrous tetrahydrofuran were added to the solution. The mixture was stirred at the same temperature for 1.5 hours and then at 0°C. for 18 hours. The reaction mixture was neutralized with acetic acid and concentrated under reduced pressure. The residue was dissolved in a small amount of water and extracted with diethyl ether. The ethereal extracts were washed with an aqueous sodium chloride solution, dried over magnesium sulphate and concentrated under reduced pressure. The residue was distilled at 160°C. under a pressure of 0.7 mm Hg to remove the non-reacted impurities. The resulting residue was purified by column chromatography on silica gel using a mixture of ethyl acetate and cyclohexane (5:1) as eluent to give 26 g. of the title compound having the following physical characteristics:

IR (liquid film):$\nu$;
  1730, 1590, 1450, 1050 – 1030, 750 cm$^{-1}$;
NMR (CCl$_4$ solution):$\delta$
  7.50 – 6.70 (4H, m), 4.70 (2H, s), 3,65 (6H, d), 3.10 (2H, d).

REFERENCE EXAMPLE 12

Methyl 9α-acetoxy-11α-(2-tetrahydropyranyloxy)-15-oxo-16-(3-trifluoromethylphenoxy)-ω-tetranor-prosta-cis-5,trans-13-dienoate 760 mg. of sodium hydride (65.1% content) were suspended in 100 ml. of anhydrous tetrahydrofuran. With stirring under an atmosphere of nitrogen, 9.3 g. of dimethyl 2-oxo-3-(3-trifluoromethylphenoxy)propylphosphonate (prepared as described in Reference Example 11) in 40 ml. of tetrahydrofuran were added to the suspension at 30°C. and the mixture stirred for 30 minutes.

4.5 g. of 1α-acetoxy-2α-(6-methoxycarbonyl-hex-cis-2-enyl)-3β-formyl-4α-(2-tetrahydropyranyloxy)-cyclopentane (prepared as described hereafter) in 15 ml. of tetrahydrofuran were added and the mixture stirred at 40°C. for 5 hours. The reaction mixture was then acidified with acetic acid, and silica gel was added to the mixture. The mixture was filtered, and the filtrate concentrated under reduced pressure. The residue was purified by column chromatography on silica gel using a mixture of ethyl acetate and benzene (1:8) as eluent to give 2.66 g. of the title compound having the following physical characteristics:

TLC (developing solvent, ethyl acetate - benzene = 1:8): Rf = 0.21;

IR (liquid film):ν;
  1730, 1690, 1620, 1590, 980 cm⁻¹;
NMR (CCl₄ solution):δ;
  7.59 – 6.20 (6H, m), 5.50 – 4.75 (3H, m), 4.62 (2H, s), 4.55 – 4.3 (1H, m), 3.55 (3H, s), 1.99 (3H, s).

1α-Acetoxy-2α-(6-methoxycarbonyl-hex-cis-2-enyl)-3β-formyl-4α-(2-tetrahydropyranyloxy)-cyclopentane, used as a starting material in the above procedure, was prepared from 2-oxa-3-oxo-6-syn-hydroxymethyl-7-anti-acetoxy-cis-bicyclo[3,3,0]octane, [prepared as described by E. J. Corey et al, J. Am. Chem. Soc., 92, 397, (1970)], as follows:

190 g. of 2-oxa-3-oxo-6-syn-hydroxymethyl-7-anti-acetoxy-cis-bicyclo[3,3,0]octane in 1.5 liters of absolute methanol and 130 g. of potassium hydroxide were stirred at room temperature for one hour, and then successively cooled in an ice-bath, and neutralized with hydrochloric acid. The precipitate was filtered off and the filtrate was concentrated under reduced pressure. The residue was washed with ethanol, and then with ethyl acetate,, and dried to give 124 g. of 2-oxa-3-oxo-6-syn-hydroxymethyl-7-anti-hydroxy-cis-bicyclo[3,3,-0]octane as white crystallites having the following physical characteristics: m.p.; 119°C.
IR (KBr tablet):ν;
  3350, 2970 – 2880, 1740, 1480, 1440, 1410, 1380, 1335, 1305, 1270, 1205, 1100, 1080, 1060, 1040, 1020, 1000 and 975 cm⁻¹;
NMR (in CDCl₃ + deutero dimethyl sulphoxide solution):δ;
  5.10 – 4.60 (1H, m), 4.29 (2H, s), 4.13 – 3.77 (1H, m) and 3.38 (2H, d);
TLC (developing solvent, methylene chloride:methylene chloride:methanol = 20:1): Rf = 0.27.

124 g. of 2-oxa-3-oxo-6-syn-hydroxymethyl-7-anti-hydroxy-cis-bicyclo[3,3,0]octane obtained above were dissolved in absolute pyridine (1.4 liters) and cooled to −40°C. 74 g. of acetic anhydride were added dropwise and the mixture stirred for 5 hours at −40 to −20°C. and then for 16 hours at 0°C. The pyridine was evaporated off under reduced pressure and the residue was dissolved in 1 liter of ethyl acetate. 200 g. of sodium bisulphate was added, stirred vigorously and filtered. The filtrate was concentrated under reduced pressure and the residue was purified by column chromatography on silica gel using a benzene-ethyl acetate mixture (1:3) as eluent to give 112 g. of 2-oxa-3oxo-6-syn-acetoxymethyl-7-anti-hydroxy-cis-bicyclo[3,3,0]octane as colourless needles having the following physical characteristics: m.p. 36 to 37°C.
IR (KBr tablet):ν;
  3450, 2960, 2850, 1775, 1740, 1420, 1370, 1250, 1190, 1120, 1090, 1040 and 980 cm⁻¹;
NMR (in CDCl₃):δ
  5.15 – 4.60 (1H, m), 4.3 – 3.75 (3H, m), 3.50 (1H, s) and 2.02 (3H, s);
TLC (developing solvent, methylene chloride: methanol = 20:1); Rf = 0.50.

4.3 g. of 2-oxa-3-oxo-6-syn-acetoxymethyl-7-anti-hydroxy-cis-bicyclo[3,3,0]octane, obtained above, were dissolved in 520 ml. of methylene chloride, 25 g. of dihydropyran and 0.52 g. of p-toluene-sulphonic acid were added and the mixture stirred for 20 minutes at room temperature. The reaction mixture was neutralized with an aqueous solution of sodium bicarbonate, diluted with ethyl acetate, washed with water, dried and concentrated under reduced pressure to give 56 g. of 2-oxa-3oxo-6-syn-acetoxymethyl-7-anti-(2-tetrahydropyranyloxy)-cis-bicyclo[3,3,0]octane as a colourless oil having the following physical characteristics:
IR (liquid film):ν;
  2950 – 2840, 1775, 1740, 1465, 1440, 1390 – 1340, 1240, 1180, 1140 – 1120, 1080, 1040 and 980 cm⁻¹;
NMR (in CDCl₃ solution):δ;
  5.2 – 4.72 (1H, m), 4.72 – 4.30 (1H, m), 4.2 – 3.2 (5H, m) and 2.01 (3H, s);
TLC (developing solvent, methylene chloride-methanol = 20:1): Rf = 0.74.

56 g. of the acetyl ether, prepared above, were dissolved in 900 ml. of toluene and cooled to −60°C. 456 ml. of a 25(w/v)% toluene solution of diisobutylaluminium hydride were added, stirred for 20 minutes at the same temperature; methanol was added in order to decompose the excess of diisobutylaluminium hydride and water was added. The resulting precipitate was filtered off and the filtrate was dried and concentrated under reduced pressure to give 35.2 g. of 2-oxa-3-hydroxy-6-syn-hydroxymethyl-7-anti-(2-tetrahydropyranyloxy)-cis-bicyclo-[3,3,0]octane as a colourless oil having the following physical characteristics:
IR (liquid film):ν;
  3400, 2940 – 2860, 1465 – 1440, 1380, 1355, 1325, 1260, 1200, 1140, 1120, 1075 and 1020 cm⁻¹;
TLC (developing solvent, ethyl acetate): Rf = 0.25.

37.6 g. of sodium hydride (content 63.5%) were suspended in 400 ml. of dimethyl sulphoxide and stirred at 70°C. for 1.5 hours to obtain sodiomethylsulphinylcarbanide. The reaction mixture was allowed to cool to room temperature and then added dropwise to a solution of 226 g. of 4-carboxy-n-butyl-triphenyl phosphonium bromide in 460 ml. of dimethyl sulphoxide, the reaction temperature being kept within the range 20 to 25°C.

A solution of 35.2 g. of 2-oxa-3-hydroxy-6-syn-hydroxymethyl-hyroxymethyl-7-anti-(2-tetrahydropyranyloxy)-cis-bicyclo-[3,3,0]octane, prepared above, in 90 ml. of dimethyl sulphoxide was added to the above reaction mixture and stirred at 35 to 40°C. for 1.5 hours. The reaction mixture was poured into 6 liters of ice-water and the neutral substances were removed by extraction with an ethyl acetate-diethyl ether mixture (1:1). The aqueous layer was acidified to pH 2 with saturated aqueous oxalic acid solution and extracted with a diethyl ether-n-pentane mixture (1:1). The organic layer was washed with water, dried over sodium sulphate and concentrated under reduced pressure. The residue was subjected to column chromatography on silica gel using a benzene-methanol mixture (10:1) as eluent to give 35 g. of 2α-(6-carboxy-hex-cis-2-enyl)-3β-hydroxymethyl-4α-(2-tetrahydropyranyloxy)-cyclopentan-1α-ol as a colourless oil having the following physical characteristics:
IR (liquid film):ν;
  3400, 2940 – 2860, –2300, 1710, 1450, 1435, 1400, 1355, 1245, 1200, 1140, 1120, 1075 and 1025 cm⁻¹;
NMR (in CDCl₃ solution):δ;
  6.20 (3H, s), 5.50 – 5.10 (2H, m), 4.75 – 4.36 (1H, m), 4.24 – 3.85 (2H, m) and 3.85 – 3.0 (4H, m);
TLC (developing solvent, chloroform: tetrahydrofuran:acetic acid = 10:2:1): Rf = 0.53.

To a solution of 18.8 g. 2α-(6-carboxy-hex-cis- 2-enyl)-3β-hydroxymethyl-4α-(2-tetrahydropyranyloxy)-cyclopentan-1α-ol, obtained above, in 130 ml. of diethyl ether, a freshly prepared ethereal solution of diazomethane was added with cooling in an ice-bath until the reaction mixture showed a pale yellow colour. The reaction mixture was concentrated in vacuo, and the residue was subjected to column chromatography on silica gel using a cyclohexane-ethyl acetate mixture (2:1) as eluent to give 15.4 g. of 2α-(6-methoxycarbonyl-hex-cis-2-enyl)-3β-hydroxymethyl-4α-(2-tetrahydropyranyloxy)-cyclopentan-1α-ol as a colourless oil having the following physical characteristics:
IR (liquid film):ν;
3450, 2950 – 2870, 1740, 1440, 1360, 1325, 1250, 1200, 1140, 1120, 1080 and 1025 cm⁻¹;
NMR (in CDCl₃ solution):δ;
5.55 – 5.00 (2H, m), 4.78 – 4.30 (1H, m), 4.20 – 3.06 (6H, m), 3.55 (3H, s) and 2.97 (2H, s);
TLC (developing solvent, methylene chloride:methanol = 19:1); Rf = 0.43.

13.1 g. of 2α-(6-methoxycarbonyl-hex-cis-2-enyl)-3β-hydroxymethyl-4α-(2-tetrahydropyranyloxy)-cyclopentan-1α-ol, obtained above, were dissolved in 250 ml. of absolute methylene chloride, and 25 ml. of pyridine were added. The air in the apparatus was replaced with nitrogen and the contents cooled to –20°C. To the reaction mixture was added dropwise a solution of 5.1 ml. of trimethylchlorosilane in 30 ml. of methylene chloride with stirring and stirred at the same temperature for 30 minutes. A sample of the product thus obtained had the following physical characteristic:
TLC (developing solvent, benzene-ethyl acetate = 2:1); Rf = 0.61.

A solution of 2.9 ml. of acetyl chloride in 20 ml. of methylene chloride was added dropwise to the above reaction mixture and stirred at room temperature for 30 minutes. Then 2 ml. of ethanol were added to decompose the excess of acetyl chloride. Pyridine in the reaction mixture was neutralized by the addition of 50 g. of sodium bisulphate, and the resulting precipitate was filtered off. The filtrate was concentrated under reduced pressure to give a residue having the following physical characteristic: TLC (developing solvent, benzene-ethyl acetate = 2:1); Rf = 0.82.

The residue was dissolved in 300 ml. of ethyl acetate, 100 ml. of aqueous oxalic acid solution were added and stirred vigorously at room temperature. The organic layer was separated, washed successively with water, aqueous sodium bisulphate solution, water and brine, dried with sodium sulphate and concentrated under reduced pressure to give 13.7 g. of crude product. The crude product was subjected to column chromatography on silica gel using a benzene-ethyl acetate mixture (3:1) as eluent to give 7.45 g. of 1α-actoxy-2α-(6-methoxycarbonyl-hex-cis-2-enyl)-3β-hydroxymethyl-4α-(2-tetrahydropyranyloxy)-cyclopentane, 2.40 g. of 1α-hydroxy-2α-(6-methoxycarbonyl-hex-cis-2-enyl)-3β-hydroxymethyl-4α-(2-tetrahydropyranyloxy)-cyclopentane, 720 mg. of 1α-hydroxy-2α-(6-methoxycarbonyl-hex-cis- 2-enyl)-3β-acetoxymethyl-4α-(2-tetrahydropyranyloxy)-cyclopentane, and 1.45 g. of 1α-acetoxy-2α-(6-methoxycarbonyl-hex-cis-2-enyl)-3β-acetoxymethyl-4α-(2-tetrahydropyranyloxy)-cyclopentane.

1α-Acetoxy-2α-(6-methoxycarbonyl-hex-cis-2-enyl)-3β-hydroxymethyl-4α-(2-tetrahydropyranyloxy)-cyclopentane had the following physical characteristics:
IR (liquid film):ν;
3450, 3000, 2950, 2870, 1740, 1440, 1380, 1330, 1250, 1200, 1160, 1140, 1080, 1030, 980, 920, 875 and 815 cm⁻¹;
NMR (in CDCl₃ solution):δ;
5.45 – 5.27 (2H, m), 5.16 – 4.92 (1H, m), 4.76 – 4.46 (1H, m), 4.27 – 3.96 (1H, m), 3.67 (3H, s), 2.98 – 2.64 (1H, m) and 2.05 (3H, s);
TLC (developing solvent, benzene-ethyl acetate = 2:1): Rf = 0.27.

Under an atmosphere of nitrogen, 4.4 ml. of pyridine were dissolved in 80 ml. of dichloromethane, 2.88 g. of chromium trioxide were added with stirring and then stirred for 15 minutes, 12 g. of infusorial earth were added to the reaction mixture, and then there was added a solution of 956 mg. of 1α-acetoxy-2α-(6-methoxycarbonyl-hex-cis-2-enyl)-3β-hydroxymethyl-4α-(2-tetrahydropyranyloxy)-cyclopentane (prepared as described above) in 20 ml. of dichloromethane. After stirring for 10 minutes, 20 g. of sodium bisulphate was added to the reaction mixture and stirring continued for a further 10 minutes. The resulting precipitate was filtered off and the filtrate was concentrated under reduced pressure. The residue was subjected to silica gel column chromatography using a benzene-ethyl acetate mixture (5:1) as eluent to give 1α-acetoxy-2α-(6-methoxycarbonyl-hex-cis-2-enyl)-3β-formyl-4α-(2-tetrahydropyranyloxy)-cyclopentane as a colourless oil having the following physical characteristics:
IR (liquid film):ν;
3000, 2950, 2860, 2725,, 1740, 1440 1380, 1325, 1255, 1200, 1165, 1140, 1085, 1030, 980, 920, 880 and 820 cm⁻¹;
NMR (in CDCl₃ solution):δ;
9.85–9.68 (1H, m), 5.45–4.96 (1H, m), 4.68–4.48 (1H, m), 4.48–4.25 (1H, m), 3.67 (3H, s), and 2.08 (3H, s);
TLC (developing solvent, benzene-ethyl acetate = 2:1); Rf = 0.66.

REFERENCE EXAMPLE 13 Methyl 9α-acetoxy-11α-(2-tetrahydropyranyloxy)-15α-hydroxy-16-(3-trifluoromethylphenoxy)-ω-tetranor-prosta-cis-5,trans-13-dienoate and its 15β-hydroxy isomer To a solution of 1.04 g. of methyl 9α-acetoxy-11α-(2-tetrahydropyranyloxy)-15-oxo-16-(3-trifluoromethylphenoxy)-ω-tetranor-prosta-cis-5,trans-13-dienoate (prepared as described in Reference Example 12) in 20 ml. of methanol, there was added carefully 195 mg. of sodium borohydride whilst keeping the temperature at −50°C. After 20 minutes, the mixture was neutralized with acetic acid and the methanol was evaporated under reduced pressure. The resulting mixture was extracted with ethyl acetate. The organic extracts were washed with an aqueous sodium bicarbonate solution, water and an aqueous sodium chloride solution, dried over magnesium sulphate and concentrated under reduced pressure. The residue was purified by column chromatography on silica gel using a mixture of ethyl acetate and benzene (1:4) as eluent to give 247 mg. of the 15α-hydroxy compound, 288 mg. of the 15β-hydroxy compound and 370 mg. of a mixture thereof having the following physical characteristics:
TLC (developing solvent, ethyl actate - benzene = 1:2) :
 15α-hydroxy compound : Rf = 0.42 ;
 15β-hydroxy compound : Rf = 0.47 ;
IR (liquid film):ν;

3420, 1730, 1570, 1440, 980 cm$^{-1}$;
NMR (CDCl$_3$ solution):δ;
7.60–7.00 (4H, m), 5.95–5.65 (2H, m), 5.60–5.25 (2H, m), 5.25–4.95 (1H, m), 4.80–4.40 (2H, m), 4.02 (2H, d), 3.68 (3H, s), 2.08 (3H, s).

EXAMPLE 12

9α,15α-Dihydroxy-11α-(2-tetrahydropyranyloxy)-16-(3-trifluoromethylphenoxy)-ω-tetranor-prosta-cis-5,trans-13-dienaldehyde 247 mg. of methyl 9α-acetoxy-11α-(2-tetrahyropyranyloxy)-15α-hydroxy-16-(3-trifluoromethylphenoxy)-ω-tetranor-prosta-cis-5,trans-13dienoate (prepared as described in Reference Example 13) were dissolved in 15 ml. of toluene and, after cooling to −70°C, 0.94 ml. of a 25 (w/v)% solution of diisobutylaluminium hydride in toluene was added dropwise under an atmosphere of nitrogen with stirring. After subjecting the ester to reduction for 15 minutes, the reaction mixture was treated with methanol in order to decompose the unreacted diisobutylaluminium hydride. The reaction mixture was warmed to −20°C and water was then added to the mixture. The resulting precipitate was filtered off and the filtrate was concentrated under reduced pressure to give 190 mg. of the title compound having the following physical characteristics:
TLC (developing solvent - ethyl acetate) : Rf = 0.67;
IR (liquid film) :ν;
3400, 1720, 1590, 1330, 980 cm$^{-1}$;
NMR (CDCl$_3$ solution):δ;
9.90–9.75 (1H, m), 7.70–6.80 (4H, m), 5.95–5.30 (4H, m), 4.80–4.30 (2H, m).

EXAMPLE 13

16-(3-Trifluoromethylphenoxy)-ω-tetranor-9α,11α,1-5α-trihydroxyprosta-cis-5,trans-13-dienaldehyde 160 mg. of 9α,15α-dihydroxy-11α-(2-tetrahydropyranyloxy)-16-(3-trifluoromethylphenoxy)-ω-tetranor-prosta-cis-5,trans-13-dienaldehyde (prepared as described in Example 12) were dissolved in a mixture of 3 ml. of tetrahydrofuran and 1 ml. of 1N hydrochloric acid and the reaction mixture was stirred at 45°C for one hour. The reaction mixture was extracted with ethyl acetate and the organic extracts were washed with water and an aqueous sodium chloride solution, dried over magnesium sulphate and concentrated under reduced pressure. The residue was purified by column chromatography on silica gel using a mixture of ethyl acetate and benzene as eluent to give 90 mg. of the title compound having the following physical characteristics:
TLC (developing solvent, chloroform - tetrahydrofuran - acetic acid = 10:2:1) : Rf = 0.21 ;
IR (liquid film):ν;
3360, 1725, 1590, 1450, 980 cm$^{-1}$;
NMR (CDCl$_3$ solution):δ;
9.69 (1H, t), 7.50–6.95 (4H, m), 5.75–5.15 (4H, m), 4.65–4.35 (1H, m), 4.25–3.80 (4H, m), 3.23 (3H, broad s).

REFERENCE EXAMPLE 14

Dimethyl 2-oxo-3-phenoxypropylphosphonate 40.1 g. of dimethyl methylphosphonate were dissolved in 200 ml. of anhydrous tetrahydrofuran, to which 154 ml. of a 2N n-butyllithium solution in n-hexane were added dropwise whilst maintaining the temperature from −60° to −70°C. After stirring for 20 minutes, 15 g. of ethyl phenoxyacetate in 80 ml. of tetrahydrofuran were added to the solution. The mixture was stirred at the same temperature for 2 hours and then at room temperature overnight. The reaction mixture was neutralized with acetic acid and concentrated under reduced pressure. The residue was dissolved in a small amount of water and extracted with diethyl ether. The ethereal extracts were washed with an aqueous sodium chloride solution, dried over magnesium sulphate and concentrated under reduced pressure. The residue was purified by distillation in vacuo to give 18.9 g. of the title compound having the following physical characteristics:
boiling point: 145° to 150°C/0.1 mmHg;
IR (liquid film):ν;
2950, 1740, 1600, 1500, 1250, 1040 cm$^{-1}$;
NMR (CDCl$_3$ solution):δ;
7.60–6.50 (5H, m), 5.00–4.40 (2H, broad s), 4.10–3.55 (6H, d), 3.55–2.80 (2H, d).

REFERENCE EXAMPLE 15

Methyl 9α-acetoxy-11α-(2-tetrahydropyranyloxy)-15-oxo-16-phenoxy-Ω-tetranor-prosta-cis-5,trans-13-dienoate 1.1 g. of sodium hydride (65.1% content) were suspended in 200 ml. of anhydrous tetrahydrofuran. With stirring under an atmosphere of nitrogen, 7.83 g. of dimethyl 2-oxo-3-phenoxypropylphosphonate (prepared as described in Reference Example 14) in 100 ml. of tetrahydrofuran were added to the suspension at 30°C and the mixture stirred for 30 minutes.

4.0 g. of 1α-acetoxy-2α-(6-methoxycarbonyl-hex-cis-2-enyl)-3β-formyl-4α-(2-tetrahydropyranyloxy)cyclopentane (prepared as described in Reference Example 12) in 200 ml. of tetrahydrofuran were added and the mixture stirred at 40°C for 3.5 hours. The reaction mixture was then acidified with acetic acid, and silica gel was added to the mixture. The mixture was filtered, and the filtrate concentrated under reduced pressure. The residue was purified by column chromatography on silica gel using a mixture of benzene and ethyl acetate (6:1) as eluent to give 3.82 g. of the title compound having the following physical characteristics:
TLC (developing solvent, benzene - ethyl acetate = 2:1) : Rf = 0.71;
IR (liquid film):ν; 2950, 1740, 1600, 1500, 1380, 1250 cm$^{-1}$;
NMR(CDCl$_3$ solution):δ;
7.90–6.20 (7H, m), 5.80–4.90 (3H, m), 4.90–4.35 (3H, m), 4.35–3.10 (6H, m).

REFERENCE EXAMPLE 16

Methyl 9α-acetoxy-11α-(2-tetrahydropyranyloxy)-15α-hydroxy-16-phenoxy-ω-tetranor-prosta-cis-5,trans-13-dienoate and its 15β-hydroxy isomer To a solution of 3.82 g. of methyl 9α-acetoxy-11α-(2-tetrahyropyranyloxy)-15-oxo-16-phenoxy-ω-tetranor-prosta-cis-5,trans-13-dienoate (prepared as described in Reference Example 15) in 50 ml. of methanol, there was added carefully 825 mg. of sodium borohydride whilst keeping the temperature at −40° to −30°C. After 30 minutes, the mixture was neutralized with acetic acid and the methanol was evaporated under reduced pressure. The resulting mixture was extracted with ethyl acetate. The organic extracts were washed with an aqueous sodium bicarbonate solution, water and an aqueous sodium chloride solution, dried over magnesium sulphate and concentrated under reduced pressure. The residue was purified by column chromatography on silica gel using a mixture of ethyl acetate and benzene (1:4) as eluent to give 1.42 g. of the 15α-hydroxy compound, 1.26 g. of the 15β-hydroxy compound and 870 mg. of a mixture thereof having the following physical characteristics:
TLC (developing solvent, ethyl acetate - benzene = 1:2) :
  15α-hydroxy compound : Rf = 0.42;
  15β-hydroxy compound : Rf = 0.51;
IR (liquid film):$\nu$;
  3420, 1735, 1570, 1440, 980 cm$^{-1}$;
NMR (CDCl$_3$ solution):$\delta$;
  7.65–7.00 (5H, m), 5.95–5.62 (2H, m), 5.60–5.23 (2H, m), 5.23–4.94 (1H, m), 4.85–4.40 (1H, m), 4.40–3.25 (5H, m), 3.70 (3H, s), 3.12 (2H, d), 2.08 (3H, s).

EXAMPLE 14

9α, 15α-Dihydroxy-11α-(2-tetrahydropyranyloxy)-16-phenoxy-ω-tetranor-prosta-cis-5,trans-13-dienaldehyde 1.42 g. of methyl 9α-acetoxy- 11α-(2-tetrahydropyranyloxy)-15α-hydroxy-16-phenoxy-ω-tetranor-prosta-cis-5,trans-13-dienoate (prepared as described in Reference Example 16) were dissolved in 35 ml. of toluene and, after cooling to −70°C, 3.22 ml. of a 25 (w/v)% solution of diisobutylaluminum hydride in toluene were added dropwise under an atmosphere of nitrogen with stirring. After subjecting the ester to reduction for 15 minutes, the reaction mixture was treated with methanol in order to decompose the unreacted diisobutylaluminium hydride. The reaction mixture was warmed to −20°C and water was added to the mixture. The resulting precipitate was filtered off and the filtrate was concentrated under reduced pressure to give 950 mg. of the title compound having the following physical characteristics:
TLC (developing solvent, ethyl acetate) : Rf = 0.69;
IR (liquid film):$\nu$;
  3420, 1720, 1600, 1335, 980 cm$^{-1}$;
NMR (CDCl$_3$ solution):$\delta$;
  9.90–9.70 (1H, m), 7.70–7.00 (5H, m), 5.95–5.32 (4H, m),
  4.80–4.30 (1H, m).

EXAMPLE 15

9α, 11α, 15α-Trihydroxy-16-phenoxy-ω-tetranor-prosta-cis-5, trans-13-dienaldehyde 480 mg. of 9α, 15α-dihydroxy-11α-(2-tetrahydropyranyloxy)-16-phenoxy-ω-tetranor-prosta-cis-5,trans-13-dienaldehyde (prepared as described in Example 14) were dissolved in a mixture of 9 ml. of tetrahydrofuran and 3 ml. of 1N hydrochloric acid and the reaction mixture was stirred at 45°C for 1 hour. The reaction mixture was extracted with ethyl acetate and the organic extracts were washed with water and an aqueous sodium chloride solution, dried over magnesium sulphate and concentrated under reduced pressure. The residue was purified by column chromatography on silica gel using a mixture of ethyl acetate and benzene (1:2) as eluent to give 278 mg. of the title compound having the following physical characteristics:
TLC (developing solvent, chloroform - tetrahydrofuran - acetic acid = 10:2:1) : Rf = 0.23 ;
IR (liquid film):$\nu$;
  3350, 2940, 1725, 1595, 1450, 980 cm$^{-1}$;
NMR (CDCl$_3$ solution):$\delta$;
  9.68 (1H, t), 7.50–6.90 (5, m), 5.72–5.15 (4H, m), 4.65–4.33 (1H, m), 4.24–3.80 (4H, m), 3.20 (3H, broad s).

REFERENCE EXAMPLE 17

2-Oxa-3-oxo-6-syn-[3-oxo-4-(3-trifluoromethylphenoxy)-but-trans-1-enyl]-7-anti-acetoxy-cis-bicyclo[3,3,0]-octane 2.2 g. of sodium hydride (63% content) were suspended in 380 ml. of tetrahydrofuran, and a solution of 20 g. of dimethyl 2-oxo-3-(3-trifluoromethylphenoxy)-propylphosphonate (prepared as described in Reference Example 11) in 50 ml. of tetrahydrofuran was added. Hydrogen was vigorously generated and the solution became a clear yellow. To the solution obtained a solution of 17 g. of 2-oxa-3-oxo-6-syn-formyl-7-anti-acetoxy-cis-bicyclo[3,3,0]octane (prepared as described in Reference Example 3) in 40 ml. of tetrahydrofuran was added and the reaction mixture was stirred at 0° to −5°C. for 2.5 hours. It was then neutralized with acetic acid and the resulting precipitate removed by filtration. The filtrate was concentrated under reduced pressure, and the residue was purified by column chromatography on silica gel using a mixture of ethyl acetate and benzene (1:4) as eluent to give 14.2 g. of the title compound having the following physical characteristics:
TLC (developing solvent, ethyl acetate - benzene = 1:4); Rf = 0.52;
NMR (CDCl$_3$ and CCl$_4$ solution) :$\delta$;
  7.65–6.15 (6H, m), 5.35–4.50 (4H, m), 1.97 (3H, s).

REFERENCE EXAMPLE 18

2-Oxa-3-oxo-6-syn-[3(\)-hydroxy-4-(3-trifluoromethylphenoxy)-but-trans-1-enyl]-7-anti-acetoxy-cis-bicyclo-[3,3,0]octane 13.9 g. of 2-oxa-3-oxo-6-syn-[3-oxo-4-(3-trifluoromethylphenoxy)-but-trans-1-enyl]-7-anti-acetoxy-cis-bicyclo[3,3,0]octane (prepared as described in Reference Example 17) were dissolved in 150 ml. of methanol, and 3.2 g. of sodium borohydride were added whilst maintaining the internal temperature at −40°C. After stirring at −40° to −30°C, for 15 minutes, the mixture was neutralized with acetic acid and then concentrated under reduced pressure. The resulting residue was dissolved in ethyl acetate, and the solution was washed successively with an aqueous solution of sodium bicarbonate and an aqueous solution of sodium chloride and dried over magnesium sulphate. The solvent was distilled off and the residue was purified by column chromatography on silica gel using a mixture of benzene and ethyl acetate (10 to 7:1) as eluent to give 12.8 g. of the title compound having the following physical characteristics:
IR (liquid film):$\nu$;
  3450, 2930, 2855, 1775, 1740, 1600, 1500, 1450, 1340, 1250, 1170, 1030, 1075, 980 cm$^{-1}$;
NMR (CDCl$_3$ solution):$\delta$;
  7.65–6.90 (4H, m), 5.90–5.55 (2H, s), 5.25–4.72 (2H, m), 4.72–4.30 (1H, m), 3.98 (2H, s), 3.20–2.70 (1H, broad s), 2.02 (3H, s);
TLC (developing solvent, methylene chloride - methanol = 20:1); Rf = 0.43.

REFERENCE EXAMPLE 19

2-Oxa-3-oxo-6-syn-[3(\)
-hydroxy-4-(3-trifluoromethylphenoxy)-but-trans-1-enyl]-7-anti-hydroxy-cis-bicyclo[3,3,0]octane 8.3 g. of 2-oxa-3-oxo-6-syn[3(\)
-hydroxy-4-(3-trifluoromethylphenoxy)-but-trans-1-enyl]-7-anti-acetoxy-cis-bicyclo[3,3,0]octane (prepared as described in Reference Example 18), 2.764 g. of potassium carbonate and 70 ml. of methanol were mixed and stirred at room temperature for 30 minutes. The reaction mixture was neutralized with 1N hydrochloric acid and extracted with ethyl acetate. The extracts were washed with an aqueous solution of sodium chloride, dried over magnesium sulphate and concentrated under reduced pressure. The residue was purified by column chromatography on silica gel using a mixture of benzene and ethyl acetate (1:3) as eluent to give 5.9 g. of the title compound having the following physical characteristics:
IR (liquid film):$\nu$;
  3400, 3060, 2940, 2860, 1770, 1600, 1500, 1455, 1380, 1340, 1250, 1170, 1130, 1075, 1045, 980 cm$^{-1}$;
NMR (CDCl$_3$ solution):$\delta$;
  7.60–6.80 (4H, m), 5.85–5.48 (2H, m), 5.10–4.65 (1H, m), 4.65–4.20 (1H, m), 4.20–3.10 (5H, m),
TLC (developing solvent, ethyl acetate - benzene 3:1, twice); Rf = 0.42.

REFERENCE EXAMPLE 20

2-Oxa-3-oxo-6-syn-[3(\)
-hydroxy-4-(3-trifluoromethylphenoxy)-butyl]-7-anti-hydroxy-cis-bicyclo[3,3,0]-octane 300 mg. of palladium on charcoal were suspended in 30 ml. of methanol. Air in the apparatus was replaced by hydrogen and a solution of 3.254 g. of 2-oxa-3-oxo-6-syn-[3(\)
-hydroxy-4-(3-trifluoromethylphenoxy)-but-trans-1-enyl]-7-anti-hydroxy-cis-bicyclo[3,3,0]octane (prepared as described in Reference Example 19) in 20 ml. of methanol were added. Catalytic reduction of the compound was carried out at room temperature under ambient pressure for 1 hour. After completion of the reaction, the catalyst was separated by filtration and the filtrate was evaporated to dryness under reduced pressure to give 3.02 g. of the title compound having the following physical characteristics:
IR (liquid film):$\nu$;
  3370, 3060, 2920, 2850, 1760, 1600, 1495, 1450, 1335, 1300, 1240, 1170, 1125, 1070, 1040 cm$^{-1}$;
NMR (CDCl$_3$ solution):$\delta$;
  7,50–6.82 (4H, m), 5.10–4.75 (1H, m), 4.30–3.58 (4H, m), 3.25–2.80 (2H, broad s).

REFERENCE EXAMPLE 21

2-Oxa-3-oxo-6-syn-[3(\)
-(2-tetrahydropyranyloxy)-4-(3-trifluoromethylphenoxy)-butyl]-7-anti-(2-tetrahydropyranyloxy)-cis-bicyclo[3,3,0]octane 3.02 g. of 2-oxa-3-oxo-6-syn-[3(\)
-hydroxy-4-(3-trifluoromethylphenoxy)-butyl]-7-anti-hydroxy-cis-bicyclo[3,3,0]octane (prepared as described in Reference Example 20) were dissolved in 9.3 ml. of methylene chloride, and the solution was reacted with 2.0 ml. of dihydropyran and 17.3 mg. of p-toluene sulphonic acid at 18° to 25°C. for 15 minutes to give 4.7 g. of the title compound having the following physical characteristics:
IR (liquid film):$\nu$;
  2940, 2850, 1770, 1595, 1495, 1440, 1330, 1240, 1200, 1170, 1135, 1075, 1035 cm$^{-1}$;
NMR (CDCl$_3$ solution):$\delta$;
  7.60–6.90 (4H, m), 5.20–4.40 (3H, m), 4.40–3.20 (8H, m);
TLC (developing solvent, methylene chloride - methanol = 19:1); Rf = 0.90.

REFERENCE EXAMPLE 22

2-Oxa-3-hydroxy-6-syn-[3(\)
-(2-tetrahydropyranyloxy)-4-(3-trifluoromethylphenoxy)-butyl]-7-anti-(2-tetrahydropyranyloxy)-cis-bicyclo[3,3,0]octane 4.7 g. of 2-oxa-3-oxo-6-syn-[3(\)
-(2-tetrahydropyranyloxy)-4-(3-trifluoromethylphenoxy)-butyl]-7-anti-(2-tetrahydropyranyloxy)-cis-bicyclo-[3,3,0]octane (prepared as described in Reference Example 21) were reduced at −50° to −60°C. for 30 minutes using 12.5 ml. of a 25 (w/v)% solution of diisobutylaluminium hydride in toluene to give 4.4 g. of the title compound having the following physical characteristics:
IR (liquid film):$\nu$ :
  3400, 2920, 2850, 1590, 1490, 1440, 1330, 1285, 1235, 1200, 1165, 1130, 1070, 1030 cm$^{-1}$;
NMR (CDCl$_3$ solution):$\delta$; 7.60–6.90 (4H, m), 5.70–5.30 (1H, broad s), 5.00–4.30 (3H, m), 4.30–3.0 (9H, m),
TLC (developing solvent, methylene chloride - methanol = 19:1); Rf = 0.43.

REFERENCE EXAMPLE 23

Methyl 9$\alpha$-hydroxy- 11$\alpha$,15(\)
-bis-(2-tetrahydropyranyloxy)-16-(3-trifluoromethylphenoxy)-$\omega$-tetranor-prost-cis-5-enoate A solution of 21.5 g. of 4-hydroxycarbonyl-n-butyl-triphenylphosphonium bromide in 40 ml. of dimethyl sulphoxide were mixed with a solution of sodiomethyl-sulphinyl carbanide, prepared from 3.6 g. of sodium hydride (63% content) and 50 ml. of dimethyl sulphoxide, whilst maintaining the temperature below 25°C. The solution became scarlet about half way through the addition. A solution of 4.4 g. of 2-oxa-3-hydroxy-6-syn-[3(\)
-(2-tetrahydropyranyloxy)-4-(3-trifluoromethylphenoxy)-butyl]-7-anti-(2-tetrahydropyranyloxy)-cis-bicyclo[3,3,0]octane (prepared as described in Reference Example 22) in 20 ml. of dimethyl sulphoxide were added, and the mixture stirred vigorously at room temperature for one hour. The reaction mixture was poured into 800 ml. of ice-water and neutral substances were removed by extraction with a mixture of ethyl acetate and diethyl ether (1:1). The aqueous layer was acidified to pH 2 with a saturated aqueous oxalic acid solution and extracted with a mixture of diethyl ether and n-pentane (1:1). The extracts were washed with water, dried over magnesium sulphate and concentrated under reduced pressure to give crude 9$\alpha$-hydroxy-11$\alpha$, -15 (\)

-bis-(2-tetrahydropyranyloxy)-16-(3-trifluoromethylphenoxy)-ω-tetranor-prost-cis-5-enoic acid having the following physical characteristics: TLC (developing solvent, methylene chloride - methanol = 19:1); Rf = 0.40.

To a solution of the crude acid, obtained above, in 40 ml. of diethyl ether, a freshly prepared ethereal solution of diazomethane was added with cooling in an ice bath until the reaction mixture showed a pale yellow colour. The reaction mixture was concentrated in vacuo, and the residue was subjected to column chromatography on silica gel using a mixture of cyclohexane and ethyl acetate (2:1) as eluent to give 3.984 g. of the title compound having the following physical characteristics:
IR (liquid film):ν;
 3500, 2940, 2850, 1740, 1595, 1495, 1450, 1335, 1250, 1205, 1170, 1130, 1080, 1070, 1035 cm$^{-1}$;
NMR (CCl$_4$ solution):δ;
 7.50–6.80 (4H, m), 5.75–5.00 (2H, m), 5.00–4.40 (2H, m), 4.40–3.00 (9H, m), 3.60 (3H, s).
TLC (developing solvent, methylene chloride - methanol = 19:1); Rf = 0.67.

EXAMPLE 16

9α-Hydroxy-11α,15(\)

-bis-(2-tetrahydropyranyloxy)-16-(3-trifluoromethylphenoxy)-ω-tetranor-prost-cis-5-enaldehyde 500 mg. of methyl 9α-hydroxy-11α,15(\)
-bis-(2-tetrahydropyranyloxy)-16-(3-trifluoromethylphenoxy)-ω-tetranor-prost-cis-5-enoate (prepared as described in Reference Example 23) were dissolved in 15 ml. of toluene and, after cooling to −60° to −55°C., 1.0 ml. of a 25(w/v)% solution of diisobutylaluminium hydride in toluene was added dropwise under an atmosphere of nitrogen with stirring. After subjecting the ester to reduction for 15 minutes, the reaction mixture was treated with methanol in order to decompose the unreacted diisobutylaluminum hydride. The reaction mixture was warmed to −20°C. and water was then added to the mixture. The resulting precipitate was filtered off and the filtrate was concentrated under reduced pressure to give 460 mg. of the title compound having the following physical characteristics:
IR (liquid film):ν;
 3450, 2930, 1725, 1595, 1490, 1445, 1330, 1240, 1200, 1180, 1130, 1080, 1035 cm$^{-1}$;
NMR (CDCl$_3$ solution):δ;
 9.80 (1H, s), 7.70–6.80 (4H, m), 5.75–5.00 (2H, m), 5.00–4.50 (2H, m), 4.50–3.20 (9H, m);
TLC (developing solvent, methylene chloride - methanol = 19:1); Rf = 0.48.

EXAMPLE 17

9α,11α,15(\)

-Trihydroxy-16-(3-trifluoromethylphenoxy)-ω-tetranor-prost-cis-5-enaldehyde 460 mg. of 9α-hydroxy-11α,15(\)
-bis-(2-tetrahydropyranyloxy)-16-(3-trifluoromethylphenoxy)-ω-tetranor-prost-cis-5-enaldehyde (prepared as described in Example 16) were dissolved in a mixture of 5 ml. of tetrahydrofuran and 2 ml. of 1N hydrochloric acid and the reaction mixture was stirred at 40° to 45°C. for one hour. The reaction mixture was extracted with ethyl acetate and the organic extracts were washed with water and an aqueous solution of sodium chloride, dried over magnesium sulphate and concentrated under reduced pressure. The residue was purified by column chromatography on silica gel using a mixture of ethyl acetate and cyclohexane (1:1) as eluent to give 290 mg. of the title compound having the following physical characteristics:
IR (liquid film):ν;
 3400, 2850, 2720, 1595, 1495, 1450, 1380, 1335, 1250, 1175, 1130, 1070, 1050 cm$^{-1}$;
NMR (CDCl$_3$ solution):δ;
 9.745 (1H, t), 7.50–6.90 (4H, m), 5.70–5.00 (2H, m), 4.30–3.55 (5H, m), 3.55–2.83 (3H, broad s), 2.45 (2H, t-d);
TLC (developing solvent, chloroform - tetrahydrofuran - acetic acid = 10:2:1); Rf = 0.29.

REFERENCE EXAMPLE 24

Methyl 9α-hydroxy-11α,15(\)

-bis-(2-tetrahydropyranyloxy)-16-(3-trifluoromethylphenoxy)-ω-tetranor-prostanoate 300 mg. of palladium on charcoal were suspended in 30 ml. of methanol. Air in the apparatus was replaced by hydrogen and a solution of 500 mg. of methyl 9α-hydroxy-11α,15(\)
-bis-(2-tetrahydropyranyloxy)-16-(3-trifluoromethylphenoxy)-ω-tetranor-prost-cis-5-enoate (prepared as described in Reference Example 23) in 20 ml. of methanol was added. Catalytic reduction was carried out at room temperature under ambient pressure for 1 hour. After completion of the reaction, the catalyst was separated by filtration and the filtrate was evaporated to dryness under reduced pressure to give 467 mg. of the title compound having the following physical characteristics:
IR (liquid film): ν;
 3500, 2940, 2850, 1740, 1600, 1495, 1450, 1340, 1250, 1205, 1170, 1130, 1085, 1070, 1035 cm$^{-1}$;
NMR (CDCl$_3$ solution): δ;
 7.70–6.90 (4H, m), 5.10–4.50 (2H, m), 4.50–3.20 (6H, m), 4.10 (1H, m), 3.70 (3H, s);
TLC (developing solvent, methylene chloride - methanol = 19:1; plate: silica gel impregnated with silver nitrate); Rf = 0.61, Rf of the starting material = 0.51.

EXAMPLE 18

9α-Hydroxy-11α,15(\)

-bis-(2-tetrahydropyranyloxy)-16-(3-trifluoromethylphenoxy)-ω-tetranor-prostanaldehyde 467 mg. of methyl 9α-hydroxy-11α,15(\)
-bis-(2-tetrahydropyranyloxy)-16-(3-trifluoromethylphenoxy)-ω-tetranor-prostanoate (prepared as described in Reference Example 24) were dissolved in 10 ml. of toluene and, after cooling to −60° to −50°C, 1.0 ml. of a 25(w/v)% solution of diisobutylaluminum hydride in toluene was added dropwise under an atmosphere of nitrogen with stirring. After subjecting the ester to reduction for 15 minutes the reaction mixture was treated with methanol in order to decompose the unreacted diisobutylaluminum hydride. The reaction mixture was warmed to −20°C. and water was then added to the mixture. The resulting precipitate was filtered off and the filtrate was concentrated under reduced pressure to give 397 mg. of the title compound having the following physical characteristics:
IR (liquid film): ν;
 3450, 2920, 2850, 1720, 1595, 1495, 1450, 1390, 1340, 1245, 1210, 1170, 1135, 1075, 1030 cm$^{-1}$;
NMR (CDCl$_3$ solution): δ;

9.80 (1H, s), 7.65–6.90 (4H, m), 5.00–4.50 (2H, m), 4.07 (2H, m), 4.50–3.30 (7H, m);
TLC (developing solvent, methylene chloride - methanol = 19:1); Rf = 0.52.

EXAMPLE 19

9α,11α,15(∽)-Trihydroxy-16-(3-trifluoromethylphenoxy)-ω-tetranor-prostanaldehyde 397 mg. of 9α-hydroxy-11α,15(∽)-bis-(2-tetrahydropyranyloxy)-16-(3-trifluoromethylphenoxy)-ω-tetranor-prostanaldehyde (prepared as described in Example 18) were dissolved in a mixture of 5 ml. of tetrahydrofuran and 4 ml. of 1N hydrochloric acid and the reaction mixture was stirred at 40°C. for one hour. The reaction mixture was extracted with ethyl acetate and the organic extracts were washed with water and an aqueous sodium chloride solution, dried over magnesium sulphate and concentrated under reduced pressure. The residue was purified by columnn chromatography on silica gel using a mixture of ethyl acetate and n-hexane (1:1) as eluent to give 191 mg. of the title compound having the following physical characteristics:
IR (liquid film):ν;
  3350, 2910, 2840, 1720, 1595, 1495, 1450, 1330, 1240, 1170, 1125, 1070, 1040 cm$^{-1}$;
NMR (CDCl$_3$ solution):δ; 9.76 (1H, t), 7.50–6.90 (4H, m), 4.30–3.70 (5H, m);
TLC (developing solvent, chloroform - tetrahydrofuran - acetic acid = 10:2:1); Rf = 0.45.

EXAMPLE 20

9α,11α,15α-Trihydroxy-prosta-cis-5,trans-13-dienaldehyde methyl acetal 116 mg. of 9α,11α,15α-trihydroxy-prosta-cis-5,trans-13-dienaldehyde (prepared as described in Example 2) were dissolved in 10 ml. of dry methanol and 310 mg. of dry oxalic acid were added to the solution at room temperature. After stirring for one hour at room temperature, 700 mg. of sodium bicarbonate were added with cooling in an ice bath to the reaction mixture, which was then concentrated to about 4 ml. The mixture was diluted with 10 ml. of water and 30 ml. of ethyl acetate with cooling in an ice bath and then separated into two layers. The aqueous layer was extracted with ethyl acetate and the organic extracts were washed with an aqueous solution of sodium chloride, dried over magnesium sulphate and concentrated under reduced pressure. The residue was purified by column chromatography on silica gel using ethyl acetate as eluent to give 120 mg. of the title compound having the following physical characteristics:
NMR (CDCl$_3$ solution): δ
  5.60–5.24 (4H, m), 4.37 (1H, t),
  4.25–3.75 (3H, m), 3.30 (6H, s);
IR (liquid film): ν; 3350, 2920, 1455, 1122, 970 cm$^{-1}$;
TLC (developing solvent, diethyl ether - tetrahydrofuran = 4:1); Rf = 0.25.

The present invention includes within its scope pharmaceutical compositions which comprise at least one new therapeutically useful compound of general formula VI, or cyclodextrin clathrato or acetal thereof, together with a pharmaceutical carrier or coating. In clinical practice the new compounds of the present invention will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the daily doses are generally between 10 μg. and 5 mg./kg. body weight by oral, intravaginal, intravenous and extraamniotic administration for contraception, menstrual regulation, abortion and the induction of labour, and between 10 μg. and 1 mg./kg. body weight by oral administration for the treatment of hypertension and disorders of the peripheral circulation. Both injectable preparations and capsules may be used.

Prostaglandin compounds according to the present invention may be administered orally by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 1 to 100 μg, and more particularly 10 to 50 μg., of active ingredient per ml. of solution are particularly suitable. The solution may contain stabilizing agents such as sodium bisulphate and buffering agents to give it an isotonic character, e.g. sodium chloride, sodium citrate and citric acid.

The active ingredients may also be administered orally by inhalation in the form of aerosols generated from self-propelling pharmaceutical compositions. Means for producing self-propelling compositions for generating aerosols for administration as medicaments are, for example, described in detail in U.S. Pat. Nos. 2,868,691 and 3,095,355.

What we claim is:

1. A compound of the formula:

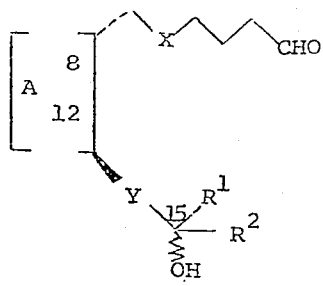

wherein A represents a grouping of the formula:

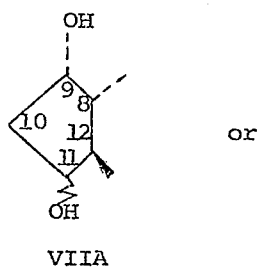 or 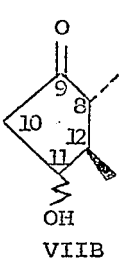

VIIA      VIIB

X represents ethylene or cis-vinylene, Y represents ethylene or trans-vinylene, $R^1$ represents a hydrogen atom or a straight- or branched-chain alkyl group containing from 1 to 4 carbon atoms, $R^2$ represents a straight- or branched-chain alkyl group containing from 1 to 10 carbon atoms or a straight- or branched-chain alkyl group containing from 1 to 4 carbon atoms substituted by a phenyl group or a cycloalkyl group containing from 5 to 7 carbon atoms or $R^2$ represents a grouping of the formula:

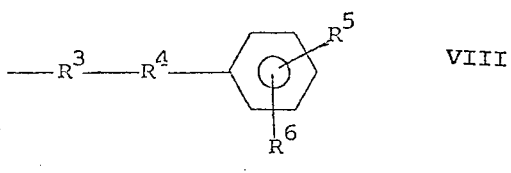

wherein $R^3$ represents a straight- or branched-chain alkylene group containing from 1 to 4 carbon atoms, $R^4$ represents an oxygen or sulphur atom or a sulphinyl group, and $R^5$ and $R^6$ each represent a hydrogen or halogen atom, a trifluoromethyl group or an alkyl group containing from 1 to 3 carbon atoms, and cyclodextrin clathrates of such aldehydes and acetal derivatives thereof with an alcohol or diol.

2. A compound according to claim 1 wherein $R^2$ represents a straight- or branched-chain alkyl group containing from 1 to 10 carbon atoms or a straight- or branched-chain alkyl group containing from 1 to 4 carbon atoms substituted by a phenyl group or a cycloalkyl group containing from 5 to 7 carbon atoms.

3. A compound according to claim 1 wherein X represents cis-vinylene.

4. A compound according to claim 1 wherein Y represents trans-vinylene.

5. A compound according to claim 1 wherein $R^2$ represents n-pentyl.

6. Prostaglandin analogues according to claim 1 wherein $R^1$ represents a hydrogen atom, and $R^2$ represents an n-pentyl group, or methyl substituted n-pentyl, a phenoxymethyl or phenylthiomethyl group or trifluoromethyl substituted phenoxymethyl or trifluoromethyl substituted phenylthiomethyl.

7. A compound according to claim 6 wherein X represents cis-vinylene.

8. A compound according to claim 6 wherein Y represents trans-vinylene.

9. A compound according to claim 6 which is 16-(3-trifluoromethylphenoxy)-ω-tetranor-9α,11α,15α-trihydroxyprosta-cis-5,trans-13-dienaldehyde.

10. A compound according to claim 1 which is 9α,11α,15α-trihydroxyprosta-cis-5,trans-13-dienaldehyde.

11. A compound according to claim 1 which is 9-oxo-11α,15α-dihydroxyprosta-cis-5,trans-13-dienaldehyde.

12. A compound according to claim 1 which is 16(R)-methyl-9α,11α,15α-trihydroxyprosta-cis-5,trans-13-dienaldehyde.

13. A compound according to claim 1 which is 16(R)-methyl-9α-oxo-11α,15α-dihydroxy-prosta-cis-5,trans-13-dienaldehyde.

14. A compound according to claim 1 which is 9α,11α,15α-trihydroxy-16-phenylthio-ω-tetranor-prosta-cis-5,trans-13-dienaldehyde.

15. A compound according to claim 1 which is 9α,11α,15α-trihydroxy-16-phenoxy-ω-tetranor-prosta-cis-5,trans-13-dienaldehyde.

16. A process for the preparation of a compound as claimed in claim 1 which comprises hydrolysing a compound of the formula:

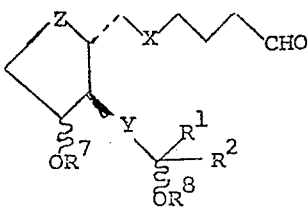 IX wherein X, Y, R¹ and R² are as defined in claim 1, Z represents

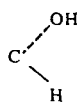

or C=O, R⁷ represents a 2-tetrahydropyranyl group unsubstituted or substituted by at least one alkyl group, or a 2-tetrahydrofuranyl or 1-ethoxyethyl group, and R⁸ represents a hydrogen atom or a 2-tetrahydropyranyl group unsubstituted or substituted by at least one alkyl group, or a 2-tetrahydrofuranyl or 1-ethoxyethyl group to convert to a hydroxy group the group OR⁷ and, when R⁸ is 2-tetrahydropyranyl group unsubstituted or substituted by at least one alkyl group, or a 2-tetrahydrofuranyl or 1-ethoxyethyl group, the group OR⁸.

17. A process according to claim 16 in which the conversion to a hydroxy group of the group OR⁷ and, when R⁸ is a 2-tetrahydropyranyl group unsubstituted or substituted by at least one alkyl group, or a 2-tetrahydrofuranyl or 1-ethoxyethyl group, the group OR⁸, is effected by mild hydrolysis with an aqueous solution of an organic acid or a dilute aqueous inorganic acid.

18. A process according to claim 17 in which the mild hydrolysis is effected in the presence of an organic solvent miscible with water.

19. A compound of the formulae:

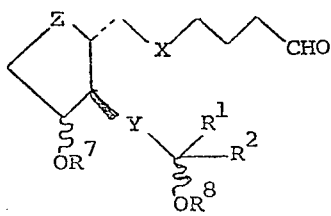 IX wherein X, Y, R¹ and R² are as defined in claim 1, Z represents

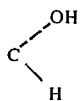

or C=O, R⁷ represents a 2-tetrahydropyranyl group unsubstituted or substituted by at least one alkyl group, or a 2-tetrahydrofuranyl or 1-ethoxyethyl group, and R⁸ represents a hydrogen atom or a 2-tetrahydropyranyl group unsubstituted or substituted by at least one alkyl group, or a 2-tetrahydrofuranyl or 1-ethoxyethyl group.

20. A compound according to claim 19 which is 9α-hydroxy-11α,15α-bis-(2-tetrahydropyranyloxy)-prosta-cis-5, trans-13-dienaldehyde.

21. A compound according to claim 19 which is 9-oxo-11α,15α-bis-(2-tetrahydropyranyloxy)-prosta-cis-5,trans-13-dienaldehyde.

22. A compound according to claim 19 which is 16(R)-methyl-9α-hydroxy-11α,15α-bis-(2-tetrahydropyranyloxy)-prosta-cis-5,trans-13-dienaldehyde.

23. A compound according to claim 19 which is 16(R)-methyl-9-oxo-11α,15α-bis(2-tetrahydropyranyloxy)-prosta-cis-5,trans-13-dienaldehyde.

24. A compound according to claim 19 which is 9α,15α-dihydroxy-11α-(2-tetrahydropyranyl-oxy)-16-phenylthio-ω-tetranor-prosta-cis-5,trans-13-dienaldehyde.

25. A compound according to claim 19 which is 9α,15α-dihydroxy-11α-(2-tetrahydropyranyloxy)-16-(3-trifluoromethylphenoxy)-ω-tetranor-prosta-cis-5,trans-13-dienaldehyde.

26. A compound according to claim 19 which is 9α,15α-dihydroxy-11α-(2-tetrahydropyranyloxy)-16-phenoxy-ω-tetranor-prosta-cis-5,trans-13-dienaldehyde.

* * * * *